(12) United States Patent
Wu et al.

(10) Patent No.: US 8,716,499 B2
(45) Date of Patent: May 6, 2014

(54) BENZENOID COMPOUNDS OF ANTRODIA CINNAMOMEA, PREPARATION AND ANALYSIS METHOD THEREOF

(75) Inventors: Yang-Chang Wu, Kaohsiung (TW); Fang-Rong Chang, Kaohsiung (TW); Mei-Chin Lu, Pingtung County (TW); Ying-Chi Du, Chiayi (TW); Tung-Ying Wu, Kaohsiung (TW); Yu-Ming Hsu, Kaohsiung (TW)

(73) Assignee: Kaohsiung Medical University, Kaohsiung (TW)

(*) Notice: Subject to any disclaimer, the term of this patent is extended or adjusted under 35 U.S.C. 154(b) by 192 days.

(21) Appl. No.: 13/346,300

(22) Filed: Jan. 9, 2012

(65) Prior Publication Data

US 2012/0178945 A1    Jul. 12, 2012

(30) Foreign Application Priority Data

Jan. 10, 2011   (TW) .............................. 100100874 A

(51) Int. Cl.
   *C07D 317/48*   (2006.01)

(52) U.S. Cl.
   USPC ....................................................... 549/445

(58) Field of Classification Search
   USPC ....................................................... 549/445
   See application file for complete search history.

(56) References Cited

FOREIGN PATENT DOCUMENTS

| TW | 591110 | 6/2004 |
|---|---|---|
| TW | I279439 | 4/2007 |
| TW | I299665 | 8/2008 |
| TW | 201029658 | 8/2010 |

OTHER PUBLICATIONS

Chen et al., "Anti-inflammatory Benzenoids from *Antrodia camphorata*," J. Nat. Prod. vol. 70, pp. 989-992 (2007).

Shi et al., "Biologically active constituents from the fruiting body of *Taiwanofungus camphoratus*," Bioorganic and Medicinal Chemistry, vol. 19, pp. 677-683 (2011).

Chen, C., et al., "New steroid acids from *Antrodia cinnamomea*, a fungal parasite of *Cinnamomum micranthum*," J. Nat. Prod. (1995) 58(11): 1655-1661.

Chen, K., et al., "Unique formosan mushroom *Antrodia camphorata* differentially inhibits androgen-responsive LNCaP and-independent PC-3 prostate cancer cells," Nutr. Cancer, (2007) 57(1): 111-121.

Hsu et al., "*Antrodia cinnamomea* fruiting bodies extract suppresses the invasive potential of human liver cancer cell line PLC/PRF/5 through inhibition of nuclear factor kB pathway," Food Chem. Toxicol. (2007) 45(7): 1249-1257.

Liu et al., "Antihypertensive activities of a solid-state culture of *Taiwanofungus camphoratus* (Chang-chih) in spontaneously hypertensive rats," Biosci. Biotechnol. Biochem. (2007) 71(1): 23-30.

Peng et al., "*Antrodia camphorata* extract induces replicative senescence in superficial TCC, and inhibits the absolute migration capability in invasive bladder carcinoma cells," J. Ethnopharmacol. (2007) 109(1): 93-103.

Song et al., "Mycelia from *Antrodia camphorata* in Submerged culture induce apoptosis of human hepatoma HepG2 cells possibly through regulation of Fas pathway," J. Agric. Food Chem. (2005) 53(14): 5559-5564.

Wu et al., "Proteomic analysis of the effect of *Antrodia camphorata* extract on human lung cancer A549 cell," Proteomics, (2006) 6(3): 826-835.

Yang et al., "Steroids and triterpenoids of *Antodia cinnamomea*—a fungus parasitic on *Cinnamomum micranthum*," Phytochemistry, (1996) 41(5): 1389-1392.

*Primary Examiner* — Taofiq A Solola
(74) *Attorney, Agent, or Firm* — Volpe and Koenig, P.C.

(57) ABSTRACT

Disclosed are a method for preparing an n-hexane extract of the fruiting body of *Antrodia cinnamomea* (AC), wherein the fruiting body of AC is sequentially extracted with the ethanol solution and the n-hexane solution to obtain the n-hexane extract containing at least one benzenoid compound. The amounts of 4,7-dimethoxy-5-(3-methylbut-3-en-1-ynyl)-6-methyl-1,3-benzodioxole, 4,7-dimethoxy-5-methyl-1,3-benzodioxole, antrocamphine A and the combination thereof in the at least one benzenoid compound are determined using chromatography, NMR and HPLC. In addition, the present invention is applicable on detecting the amounts of benzenoid compounds in the AC healthcare food/drug or the fruiting body of AC, and thus owns the industrial values.

22 Claims, 17 Drawing Sheets

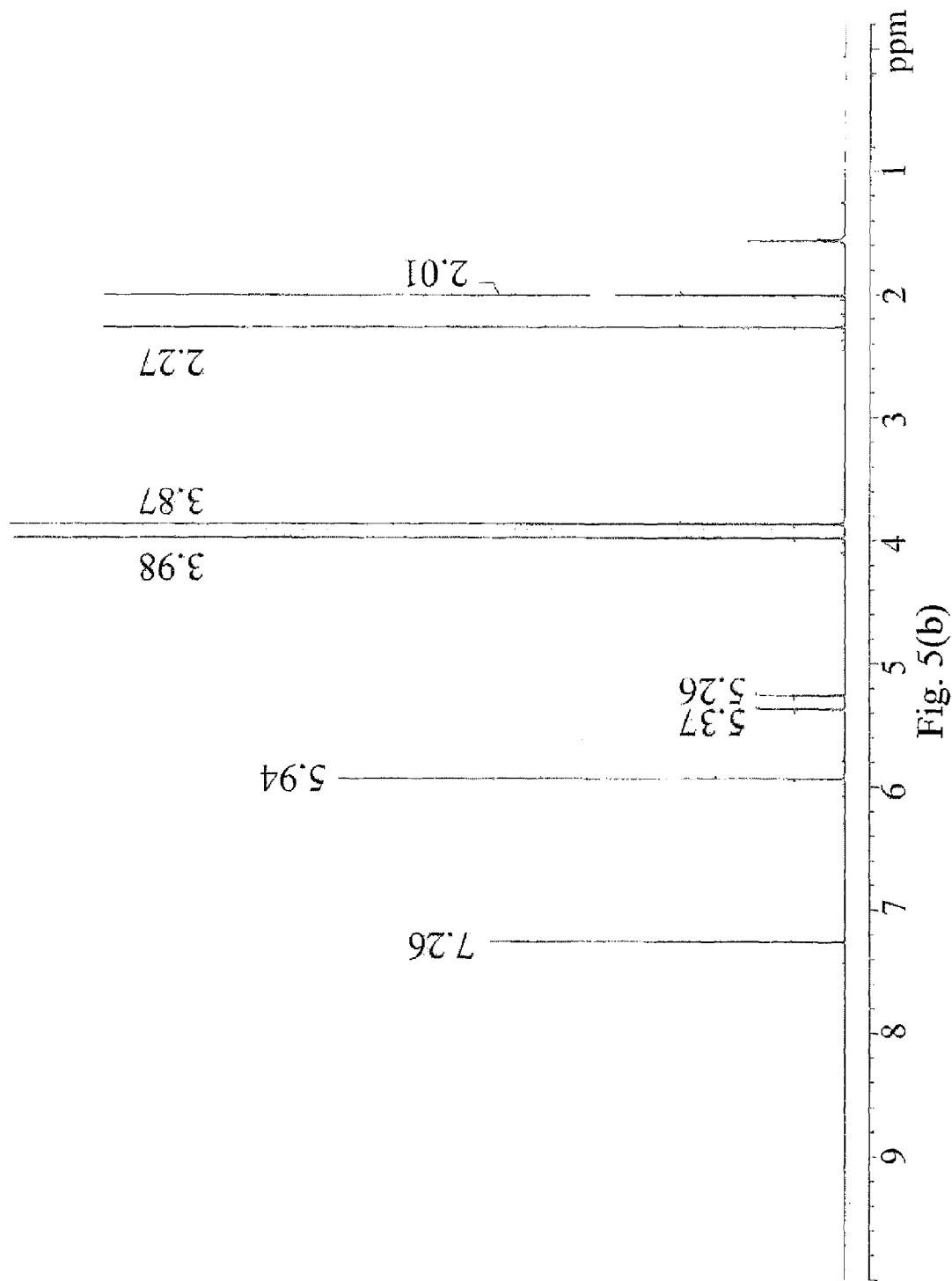

BENZENOID COMPOUNDS OF ANTRODIA CINNAMOMEA, PREPARATION AND ANALYSIS METHOD THEREOF

CROSS-REFERENCE TO RELATED APPLICATION AND CLAIM OF PRIORITY

The application claims the benefit of Taiwan Patent Application No. 100100874, filed on Jan. 10, 2011, in the Taiwan Intellectual Property Office, the disclosures of which are incorporated herein in their entirety by reference.

FIELD OF THE INVENTION

The present invention relates to an extract of the fruiting body of *Antrodia cinnamomea* (abbreviated as *A. cinnamomea* or AC). In particular, the present invention relates to the benzenoid compounds of the fruiting body of *A. cinnamomea*, the preparation method and the analysis method thereof.

BACKGROUND OF THE INVENTION

*Antrodia cinnamomea* (AC), by name niu-chang-chih or jang-jy is an endemic fungus in Taiwan and grows in the internal heartwood (or the dark/humid wood surface) of the particular *Cinnamomum kanehirai* in 400 to 2000 meters altitude. Therefore, it is uneasily to find out the wide fruiting body of AC or identify the morphological appearance of this Aphyllophorales fungus. In addition, the price of AC is still high due to their biologically active components having potential pharmaceutical value.

Since the fruiting body of AC cannot be easily found and be artificially cultured, mycelia products of AC are popular in the market and announce to own anticancer activity, reduced treatment-related symptoms and other side effects. In addition, mycelia products of AC have recently been reported to have anti-oxidant, antihypersensitive and immunostimulatory effects (Liu et al., 2007). It has been claimed of these mycelia products that they contain active components similar to the wild fruiting bodies with cytotoxic triterpenes, steroids, as well as immunostimulatory polysaccharides reported previously (Chen et al., 1995; Yang et al., 1996).

Traditionally AC has been used as health food to prevent inflammation, hypertension, itchy skin and liver cancer. Therefore, extracts of mycelia and fruiting body of AC are deemed as a potential chemotherapeutic agent against hepatoma, as well as prostate, bladder, lung cancer cells and so on (Chen et al., 2007; Hsu et al., 2007; Peng et al., 2007; Song et al., 2005; Wu et al., 2006). However, the chemical distribution and pharmacological research of niu-chang-chih products are not clarified up to now.

In addition, Taiwan Patent No. 1299665 discloses the extract of AC and the preparation thereof, in which the mycelia of AC is extracted with ethanol to obtain polysaccharides for inhibiting matrix metalloproteinase activities. However, the extract is not extracted with the fruiting body of AC, and the mycelia product thereof cannot inhibit cancer cell growth. Taiwan Patent No. 1279439 discloses that the mycelia of AC is cultured to obtain the cultured products by adjusting pH value of medium. However, there is no extraction method disclosed. Taiwan Patent No. 591110 discloses that γ-aminobutyric acid is extracted from the lyophilized mycelia of AC with water or organic solvents. However, the above-mentioned inventions did not disclose any product of the fruiting body of AC extracted with water or organic solvent, and there is no targeted second metabolites contained in the AC being identified.

It is therefore attempted by the applicant to deal with the above situation encountered in the prior art.

SUMMARY OF THE INVENTION

In the present invention, the extracts which are located in the lower polarity layer but still have activities are extracted from the fruiting body of AC, and the novel benzenoid compounds included in AC are identified. By the extraction method, the present invention can be applicable in detecting the types and amounts of benzenoid compounds in niu-chang-chih healthcare food and medicines and the fruiting body of AC, and can be used in industries.

The present invention provides a method for preparing an n-hexane extract of the fruiting body of *A. cinnamomea*, including steps of: providing the fruiting body of AC; extracting the fruiting body with an ethanol solution to obtain an ethanol extract; and extracting the ethanol extract with an n-hexane solution to obtain the n-hexane extract including at least one benzenoid compound.

The at least one benzenoid compound includes 4,7-dimethoxy-5-(3-methylbut-3-en-1-ynyl)-6-methyl-1,3-benzodioxole, 4,7-dimethoxy-5-methyl-1,3-benzodioxole and/or antrocamphine A. The preparing method further includes a step of grinding the fruiting body as fine powder.

The present invention further provides the n-hexane extract of the fruiting body of AC, which includes at least one benzenoid compound. The n-hexane extract includes characteristics that a single hydrogen signal on an aromatic ring is ranged at δ 6.4 to 6.6, a methylenedioxy signal is ranged at δ 5.8 to 6.1, a double bond signal is ranged at δ 5.4 to 5.6, a methoxy signal is ranged at δ 3.7 to 4.1 and an aromatic methyl signal is ranged at δ 2.1 to 2.6 on a $^1$H nuclear magnetic resonance ($^1$H NMR) spectrum when the n-hexane extract is solved in pyridine-D5 ($C_5D_5N$).

The n-hexane extract is obtained by sequentially extracting the fruiting body of AC with the ethanol solution and the n-hexane solution. The types of the contained at least one benzenoid compound is the same as aforementioned.

The present invention further provides an n-hexane extract of the fruiting body of AC, which includes at least one benzenoid compound. The n-hexane extract includes characteristics of having a single hydrogen signal ranged at δ 6.2 to 6.4 on an aromatic ring, a methylenedioxy signal ranged at δ 5.8 to 6.0, a double bond signal ranged at δ 5.2 to 5.5, a methoxy signal ranged at δ 3.6 to 4.1 and an aromatic methyl signal ranged at δ 2.1 to 2.4 on the $^1$H NMR spectrum when the n-hexane extract is solved in deuterium chloroform ($CDCl_3$).

The present invention further provides a method for detecting an amount of at least one benzenoid compound in the fruiting body of AC, including steps of: providing the n-hexane extract extracted from the fruiting body; detecting whether the at least one benzenoid compound is present in the n-hexane extract with the $^1$H NMR; and detecting the amount by using a high performance liquid chromatography (HPLC) when the at least one benzenoid compound is present in the n-hexane extract.

The aforementioned detecting method further including a step of detecting a signal of the at least one benzenoid compound with the $^1$H NMR, wherein the signal is one selected from a group consisting of aromatic signals, a double bond signal, a methoxy signal, a methyl signal and a combination thereof.

When the n-hexane extract is solved in $C_5D_5N$, the chemical shifts of the present signals on the $^1H$ NMR spectrum are described as above. Similarly, when solving in $CDCl_3$, the chemical shifts of the present signals on the $^1H$ NMR spectrum are also described as above.

Preferably, the HPLC used in the experiment includes a detector, and the detector is one selected from a group consisting of a full wavelength detector, a single wavelength detector and/or an electrospray ionization mass spectrometer. The full wavelength detector is configured to detect wavelengths at 254 nm and 270 nm.

The present invention further provides a method for detecting at least one benzenoid compound in the n-hexane extract of the fruiting body of AC with $^1H$ NMR based on an internal standard corresponding to the n-hexane extract, the method including steps of: detecting whether a methoxy signal ranged at δ 3.9 to 4.0 exists in the n-hexane extract; detecting whether a first methyl signal ranged at δ 2.1 to 2.2 exists in the n-hexane extract; and detecting whether a second methyl signal ranged at δ 2.3 to 2.4 exists in the n-hexane extract.

The methoxy signal, the first methyl signal and the second methyl signal are respectively present to indicate that the n-hexane extract includes 4,7-dimethoxy-5-(3-methylbut-3-en-1-ynyl)-6-methyl-1,3-benzodioxole, 4,7-dimethoxy-5-methyl-1,3-benzodioxole and an antrocamphine A.

Additionally, the first intensity of the methoxy signal is calculated based on the internal standard (pyrazine) when the methoxy signal exists. Similarly, the second intensity of the first methyl signal and/or the third intensity of the second methyl signal are calculated based on pyrazine when the first and/or the second methoxy signal exist. Furthermore, the amounts of 4,7-dimethoxy-5-(3-methylbut-3-en-1-ynyl)-6-methyl-1,3-benzodioxole, 4,7-dimethoxy-5-methyl-1,3-benzodioxole and antrocamphine A in the n-hexane extract are sequentially determined by the first, the second and the third intensities.

The present invention further provides benzenoid compounds, extracted from the fruiting body of AC, the chemical formulas of benzenoid compounds are described as the preceding paragraph.

The present invention further provides a detecting method including a step of simultaneously detecting amounts of 4,7-dimethoxy-5-(3-methylbut-3-en-1-ynyl)-6-methyl-1,3-benzodioxole, 4,7-dimethoxy-5-methyl-1,3-benzodioxole and antrocamphine A with HPLC.

The present invention further provides a detecting method including a step of detecting an amount of at least one of 4,7-dimethoxy-5-(3-methylbut-3-en-1-ynyl)-6-methyl-1,3-benzodioxole, 4,7-dimethoxy-5-methyl-1,3-benzodioxole and antrocamphine A with $^1H$ NMR.

The above objectives and advantages of the present invention will become more readily apparent to those ordinarily skilled in the art after reviewing the following detailed descriptions and accompanying drawings.

BRIEF DESCRIPTION OF THE DRAWINGS

FIGS. 5(a) to 5(d) respectively illustrate the $^1H$ NMR spectra of (a) the n-hexane extract, (b) compound 1, (c) compound 2 and (d) compound 3 solved in $CDCl_3$ at 400 MHz.

DETAILED DESCRIPTION OF THE PREFERRED EMBODIMENT

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

EXPERIMENT 1

Preparation of the n-hexane Extract of the Fruiting Body of *Antrodia cinnamomea* (AC)

Figure 1:
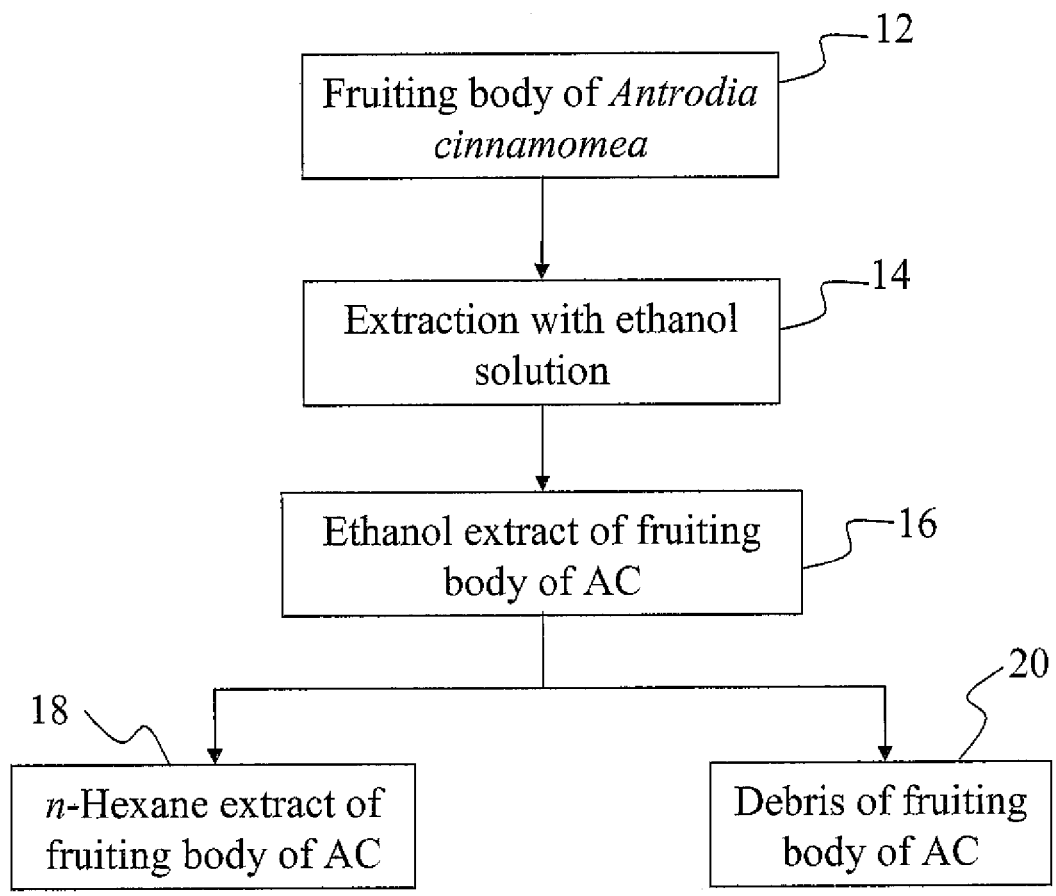
FIG. 1 illustrates a flow chart showing the preparation method of n-hexane extract of the fruiting body of *A. cinnamomea* in the present invention.

Please refer to preparation method 10 in FIG. 1, the dried fruiting body of AC was ground as fine powder (step 12), which was heated at reflux in ethanol solution at 75° C. at a ratio of 1/10 (weight/volume) (step 14). The extract was cooled, and then was precipitated at 4° C. overnight. Furthermore, the supernatant of the extract was filtered with filter paper, and the precipitate was removed by centrifuging at 3,000 rpm for 30 minutes. The extract, which was the ethanol extract of the fruiting body of AC, was lyophilized and stored at −70° C. (step 16). The ethanol extract wad extracted with n-hexane to obtain the n-hexane extract of the fruiting body of AC (hereafter abbreviated as "the n-hexane extract", step 18) and debris of the fruiting body of AC (step 20).

For exploring novel compounds in the n-hexane extract and for proving the novel compounds only existed therein rather than other extracts of the fruiting body of AC, the debris was sequentially extracted with ethyl acetate and ethanol according to the method disclosed in Taiwan Publication No. 201029658 to obtain the ethyl acetate extract and the second ethanol extract, and the n-hexane extract of the present invention was compared with the aforementioned extracts.

EXPERIMENT 2

Analysis of the NMR Spectra of the n-hexane Extract

Figure 2:
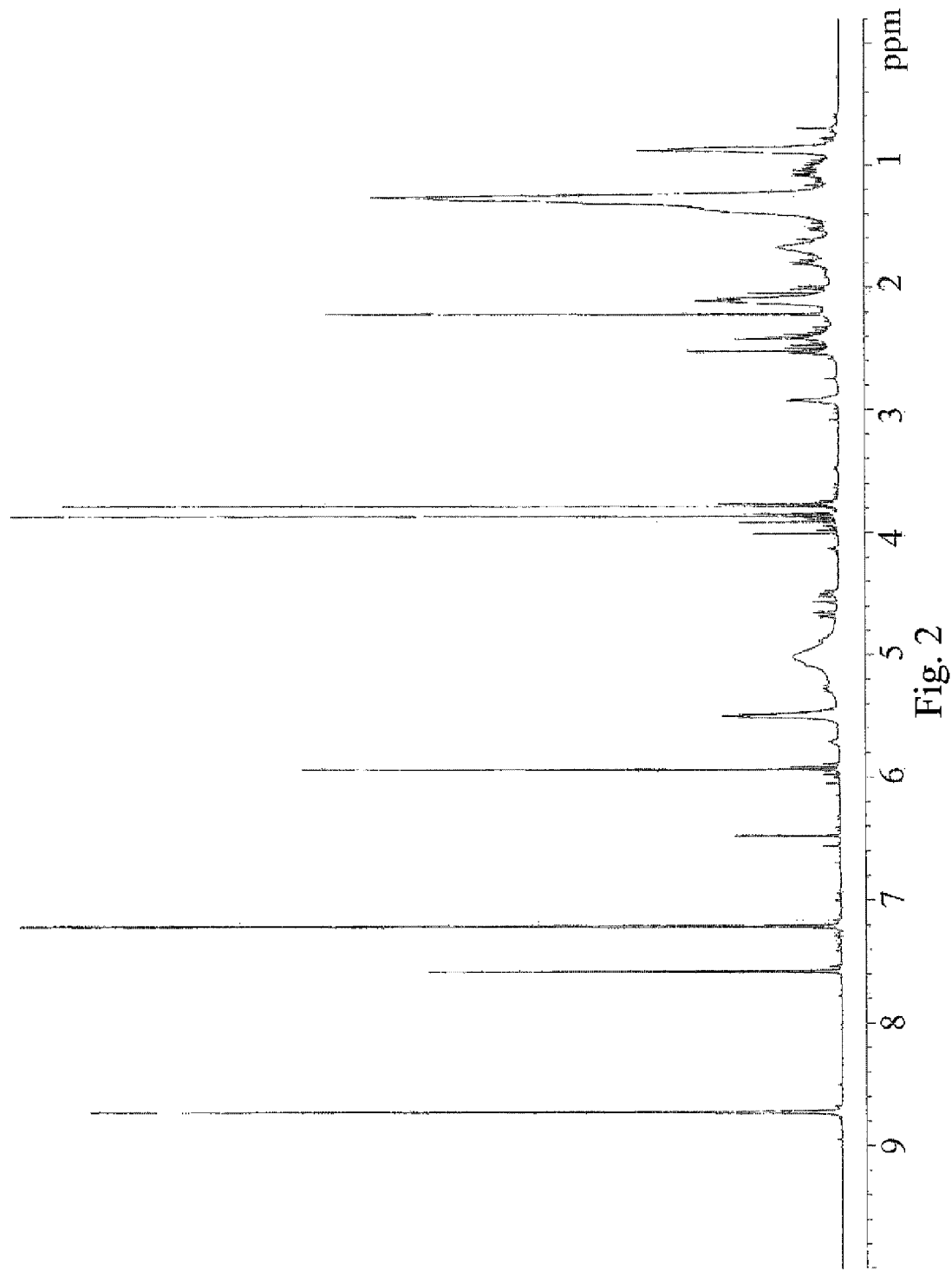
FIG. 2 illustrates the $^1H$ NMR spectrum of the n-hexane extract solved in $C_5D_5N$ at 400 MHz.

The n-hexane extract was solved in pyridine-D5 ($C_5D_5N$) as the concentration of 11.6 mg/0.75 ml, and $^1H$ NMR spectrum experiment was performed at a resolution of 400 MHz. Please refer to FIG. 2, which illustrates that the n-hexane extract has major characteristic signals of aromatic ring at δ 6.48 and 5.93 (δ 6.48 is referred to a single hydrogen signal on the aromatic ring and δ 5.93 is referred to a methylenedioxy signal), a double bond structure at δ 5.50 and methoxy signals at δ 3.87 and 3.78. However, at the same experimental conditions, the ethyl acetate extract and the second ethanol extract did not have the above characteristic signals (data not shown). Further, the n-hexane extract did not show the methyl characteristic signal of triterpenoid at the high magnetic field area, and only the long-chain structure signal was present at δ 1.27 and 0.88. Therefore, it could be determined that the n-hexane extract is the concentrated layer for the benzenoid compounds.

EXPERIMENT 3

Separation of the Components of the n-hexane Extract

Compounds 1 to 3 were extracted in the present invention, and the corresponding structural formulas (Formulas 1 to 3) of compounds 1 to 3 were detailedly listed as follows.

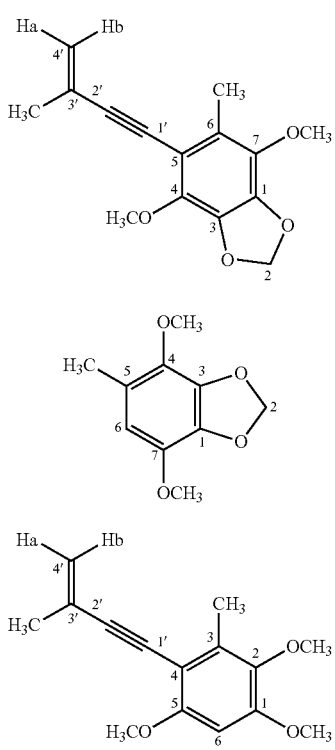

Formula 1

Formula 2

Formula 3

For distinguishing two hydrogen atoms linked to C-4' in formulas 1 and 3, both hydrogen atoms were nominated as "Ha" and "Hb", respectively.

For identifying the components of the benzenoid-concentrating layer, the n-hexane extract was separated with the column chromatography. The n-Hexane extract (897.7 mg) was chromatographed with silica gel 60 (Merck, 230 to 400 mesh) and n-hexane-ethyl acetate (EA) (1:0, 50:1, 40:1, 30:1, 20:1, 10:1, 5:1, 1:1, 0:1 sequentially) to afford 12 fractions. Each fraction product was solved in $CDCl_3$ solution, and was analyzed with $^1H$ NMR spectrum at a resolution of 200 MHz. The major characteristic signals of the aromatic components of fractions 1 and 3 were shown on the spectra and were detailedly described as follows.

Fraction 1 (245.4 mg) was chromatographed with Sephadex LH-20 resin and EA-dichloromethane ($CH_2Cl_2$) (1:1) to separate as five subfractions. Subfraction 1-4 (55.01 mg) was chromatographed with prepared-thin layer chromatography (pre-TLC) and n-hexane-EA (10:1) to afford a subfraction (47.5 mg). This subfraction (47.5 mg) then was purified with ODS high performance reverse chromatography column (250×10 mm, acetonitrile-$H_2O$ (80:20), flow rate: 2 ml/min) to give 3.3 mg of compound 2, i.e. 4,7-dimethoxy-5-methyl-1,3-benzodioxole, at retention time of 9.94 minutes, and give 3.3 mg of compound 1, i.e. 4,7-dimethoxy-5-(3-methylbut-3-en-1-ynyl)-6-methyl-1,3-benzodioxole, at retention time of 17.25 minutes.

Fraction 3 (27.7 mg) was separated with Sephadex LH-20 resin and EA-$CH_2Cl_2$ (1:1) to afford two subfractions. Subfraction 3-2 (11.8 mg) was chromatographed with pre-TLC and separated with $CH_2Cl_2$ to give 10.0 mg of compound 3, i.e. antrocamphine A, or named 1,2,5-trimethoxy-3-methyl-4-(3-methylbut-3-en-1-ynyl)benzene.

EXPERIMENT 4

Structural Characterization of the Major Components of the n-hexane Extract

Compound 1 is a white amorphous solid, and the molecular formula is $C_{15}H_{26}O_4$ using electrospray ionization mass spectrometry (ESIMS, m/z 261 [M+H]$^+$, 283 [M+Na]$^+$) and NMR spectrum. Please refer to Table 1, $^1H$ NMR spectrum of compound 1 showed two methyl signals at $\delta_H$ 2.01 (3H, s) and 2.27 (3H, s), two methoxy signals at $\delta_H$ 3.87 (3H, s) and 3.98 (3H, s), two termial olefinic methylene protons ($\delta_H$ 5.26 and 5.37) and one methylenedioxy signal at $\delta_H$ 5.94 (2H, s). By the assistance of quantum cohenrence (QC) and heteronuclear multiple-bond cohenrence (HMBC), it could be determined the signals of $^{13}C$ NMR spectrum corresponding to those of $^1H$ NMR spectrum (Table 1), and it showed an aromatic methyl signal at $\delta_C$ 13.9 (6-$CH_3$), a set of 3-methylbut-3-en-1-ynyl signals at $\delta_C$ 83.5 (C-1'), 97.5 (C-2'), 127.2 (C-3'), 121.0 ($CH_2$-4') and 23.6 (3'-$CH_3$), two methoxy signals at $\delta_C$ 60.4 (4-$OCH_3$) and 60.0 (7-$OCH_3$) and a set of benzodioxole signals at $\delta_C$ 139.5 (C-1), 101.4 ($CH_2$-2) and 136.2 (C-3).

TABLE 1

$^1H$ and $^{13}C$ NMR data of compound 1 (600 and 150 MHz of $CDCl_3$, δ: ppm, J: Hz)

| | Compound 1 | |
|---|---|---|
| Position | $\delta_H$ (J in Hz) | $\delta_C$ |
| 1 | | 139.5 (s) |
| 2 | 5.94 (2H, s) | 101.4 (t) |
| 3 | | 136.2 (s) |
| 4 | | 139.8 (s) |
| 5 | | 109.8 (s) |
| 6 | | 127.9 (s) |
| 7 | | 137.2 (s) |
| 1' | | 83.5 (s) |
| 2' | | 97.5 (s) |
| 3' | | 127.2 (s) |
| 4' | a 5.26 (1H, br s) | 121.0 (t) |
| | b 5.37 (1H, br s) | |
| 4-$OCH_3$ | 3.98 (3H, s) | 60.4 (q) |
| 6-$CH_3$ | 2.27 (3H, s) | 13.9 (q) |
| 7-$OCH_3$ | 3.87 (3H, s) | 60.0 (q) |
| 3'-$CH_3$ | 2.01 (3H, s) | 23.6 (q) |

Figure 3:
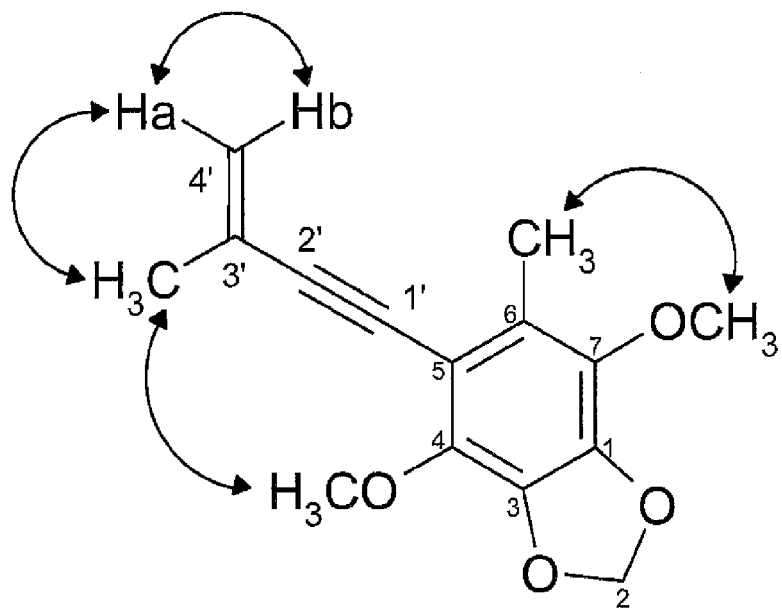
FIG. 3 illustrates a NOSEY diagram of compound 1 of the present invention.

Please refer to FIG. 3, according to the analyzed data of nuclear overhauser effect spectroscopy (NOESY) spectrum of compound 1 ($\delta_H$ 3.98 (4-OCH$_3$)/2.01 (3'-CH$_3$), $\delta_H$ 2.01 (3'-CH$_3$)/5.26 (4'-Ha), 5.26 (4'-Ha)/5.37 (4'-Hb) and 2.27 (6-OCH$_3$)/3.87 (7-OCH$_3$)), the substitutions of the benzene ring for each functional groups in compound 1 could be determined.

Figure 4:
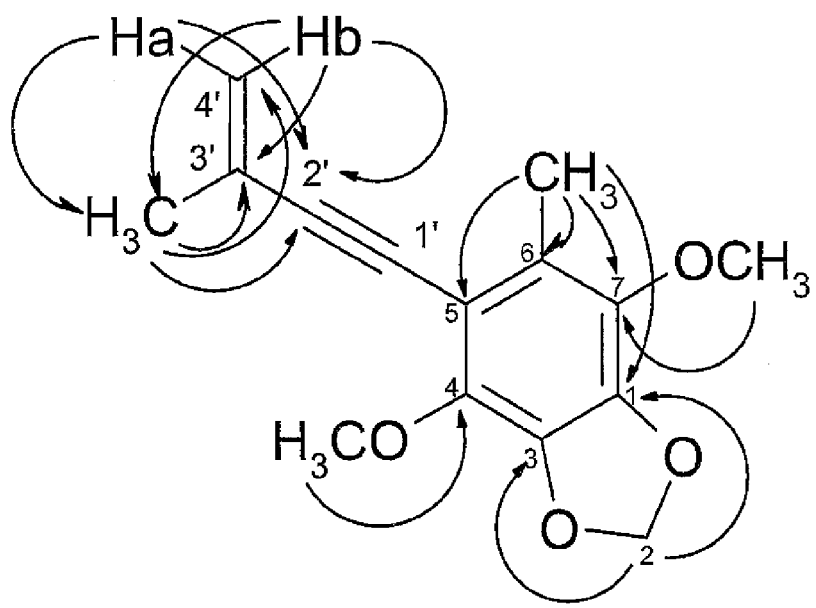
FIG. 4 illustrates a HMBC diagram of compound 1 of the present invention.

Please refer to FIG. 4, it was further determined by HMBC that a set of benzodioxole signals of compound 1 were positioned at C-1 ($\delta_C$ 139.5) and C-3 ($\delta_C$ 136.2), two methoxy signals were positioned at C-4 ($\delta_C$ 139.8) and C-7 ($\delta_C$ 137.2) respectively, a set of 3-methylbut-3-en-1-ynyl signal was positioned at C-5 ($\delta_C$ 109.8) and a methyl signal was positioned at C-6 ($\delta_C$ 127.9). Therefore, this novel compound 1 was nominated as 4,7-dimethoxy-5-(3-methylbut-3-en-1-ynyl)-6-methyl-1,3-benzodioxole.

Compound 2 is a white amorphous solid, and the molecular formula is $C_{10}H_{12}O_4$ using ESIMS (m/z 197 [M+H]$^-$) and NMR spectrum. The characteristic signals of $^1$H NMR spectrum (400 MHz of CDCl$_3$) of compound 2 showed that an aromatic methyl signal at $\delta_H$ 2.18 (3H, d, J=0.6 Hz), two methoxy signals at $\delta_H$ 3.84 (7-OCH$_3$, s) and 3.88 (4-OCH$_3$, s), a methylenedioxy signal at $\delta_H$ 5.93 (2H, s) and an aromatic single hydrogen signal at $\delta_H$ 6.30 (1H, d, J=0.6 Hz). The characteristic signals of $^{13}$C NMR (100 MHz of CDCl$_3$) showed an aromatic methyl signal at $\delta_C$ 15.9, two methoxy signals at $\delta_C$ 56.9 and 59.9, a methylenedioxy signal at $\delta_C$ 101.4. According to the analytic data of the NOESY spectrum ($\delta_H$ 3.88 (4-OCH$_3$)/2.18 (5-CH$_3$), $\delta_H$ 2.18 (5-CH$_3$)/6.30 (6-H) and 6.30 (6-H)/3.84 (7-OCH$_3$)), the substitutions on the benzene ring for each functional groups in compound 2 was determined. It could be identified six aromatic carbon signals at $\delta_C$ 134.7 (C-1), 138.6 (C-3), 136.5 (C-4), 123.7 (C-5), 108.8 (CH-6) and 138.8 (C-7) by the help of HMBC. The abovementioned structure was determined.

Compound 3 is a yellow oil, and the molecular formula is $C_{15}H_{18}O_3$ using ESIMS (m/z 247 [M+H]$^+$) and NMR spectrum. The characteristic signals of $^1$H NMR (400 MHz of CDCl$_3$) of compound 3 were two methyl signals at $\delta_H$ 2.01 (3'-CH$_3$, t, J=1.6 Hz) and 2.36 (3-CH$_3$, s), three methoxy signals at $\delta_H$ 3.72 (2-OCH$_3$, s), 3.86 (1-OCH$_3$, s) and 3.88 (5-OCH$_3$, s), two termial olefinic methylene protons ($\delta_H$ 5.25 and 5.37) and one methylenedioxy signal at $\delta_H$ 6.33 (1H, s). The characteristic signals of $^{13}$C NMR spectrum (100 MHz of CDCl$_3$) showed an aromatic methyl signal at $\delta_C$ 14.1 (3-CH$_3$), a set of 3-methylbut-3-en-1-ynyl signal at $\delta_C$ 83.5 (C-1'), 97.5 (C-2'), 127.3 (C-3'), 120.7 (CH$_2$-4') and 23.7 (3'-CH$_3$), three methoxy signals at $\delta_C$ 56.3 (1-OCH$_3$), 60.4 (2-OCH$_3$) and 55.8 (5-OCH$_3$), and six aromatic carbon signals at $\delta_C$ 157.2 (C-1), 141.1 (C-2), 135.3 (C-3), 104.8 (C-4), 153.4 (C-5) and 94.4 (CH-6). The aforementioned chemical structure of compound 3 could be determined by the assistance of NOSEY and HMBC.

EXPERIMENT 5

Comparison of NMR of the n-hexane Extract with its Major Components

Figure 5A:
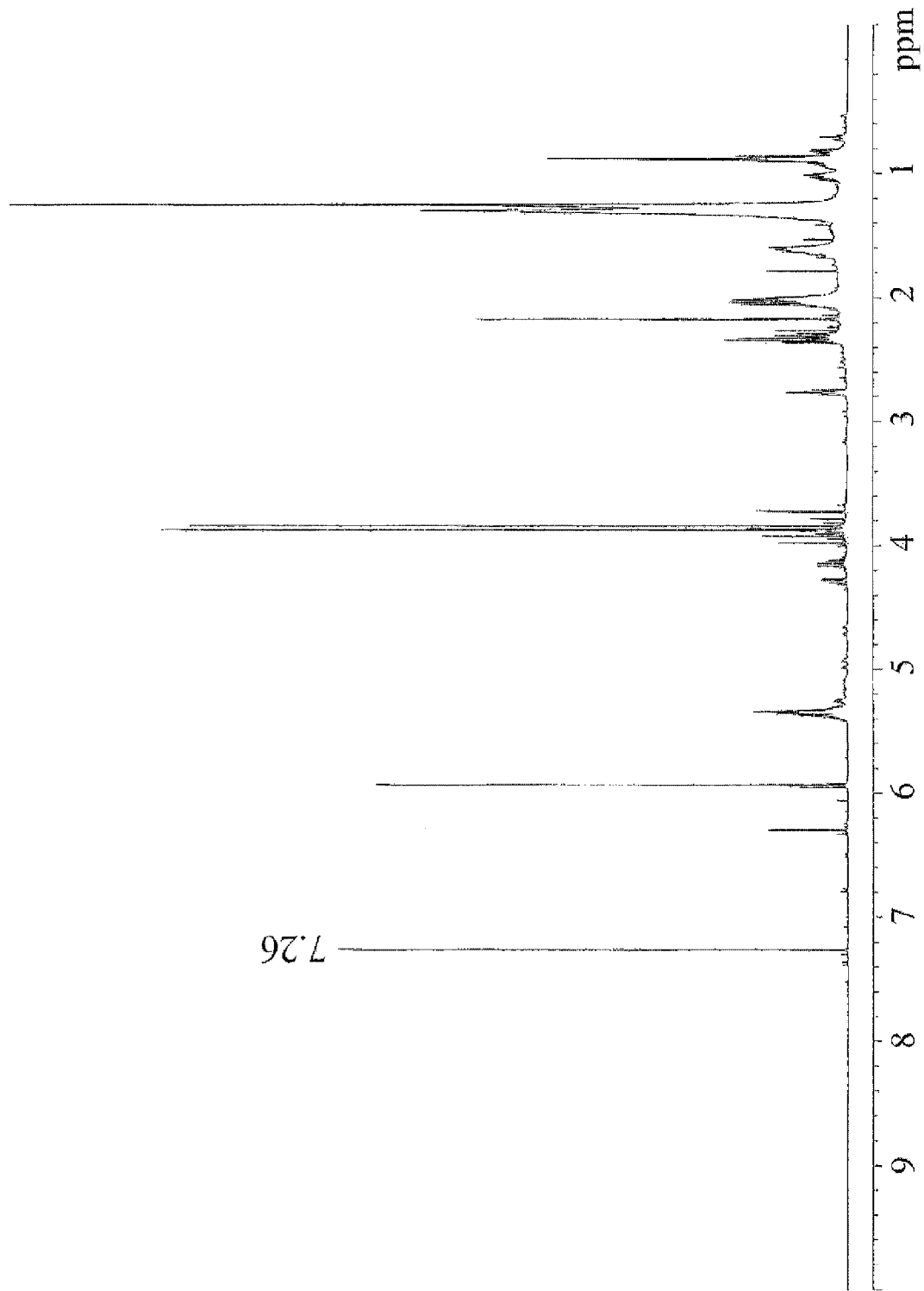
Figure 5C:
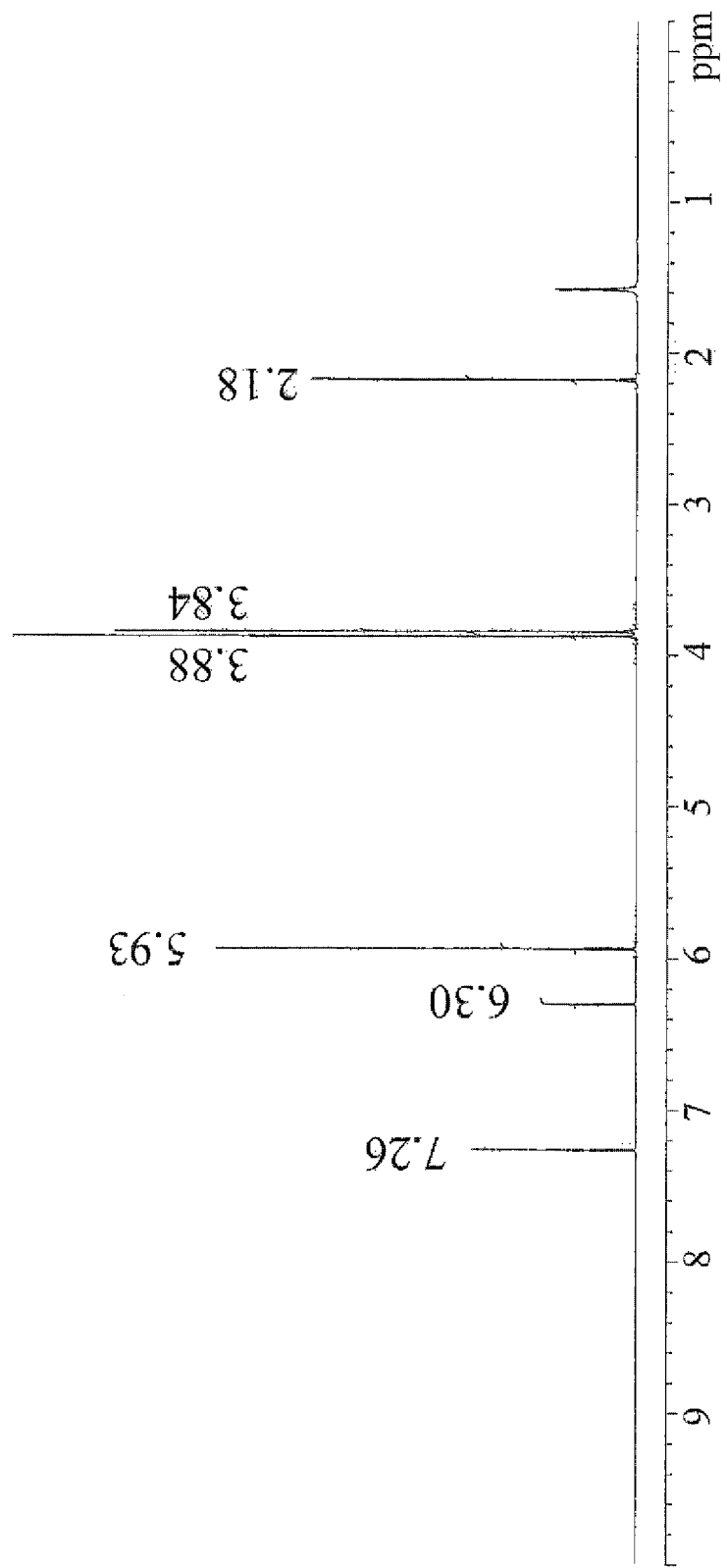
Figure 5D:
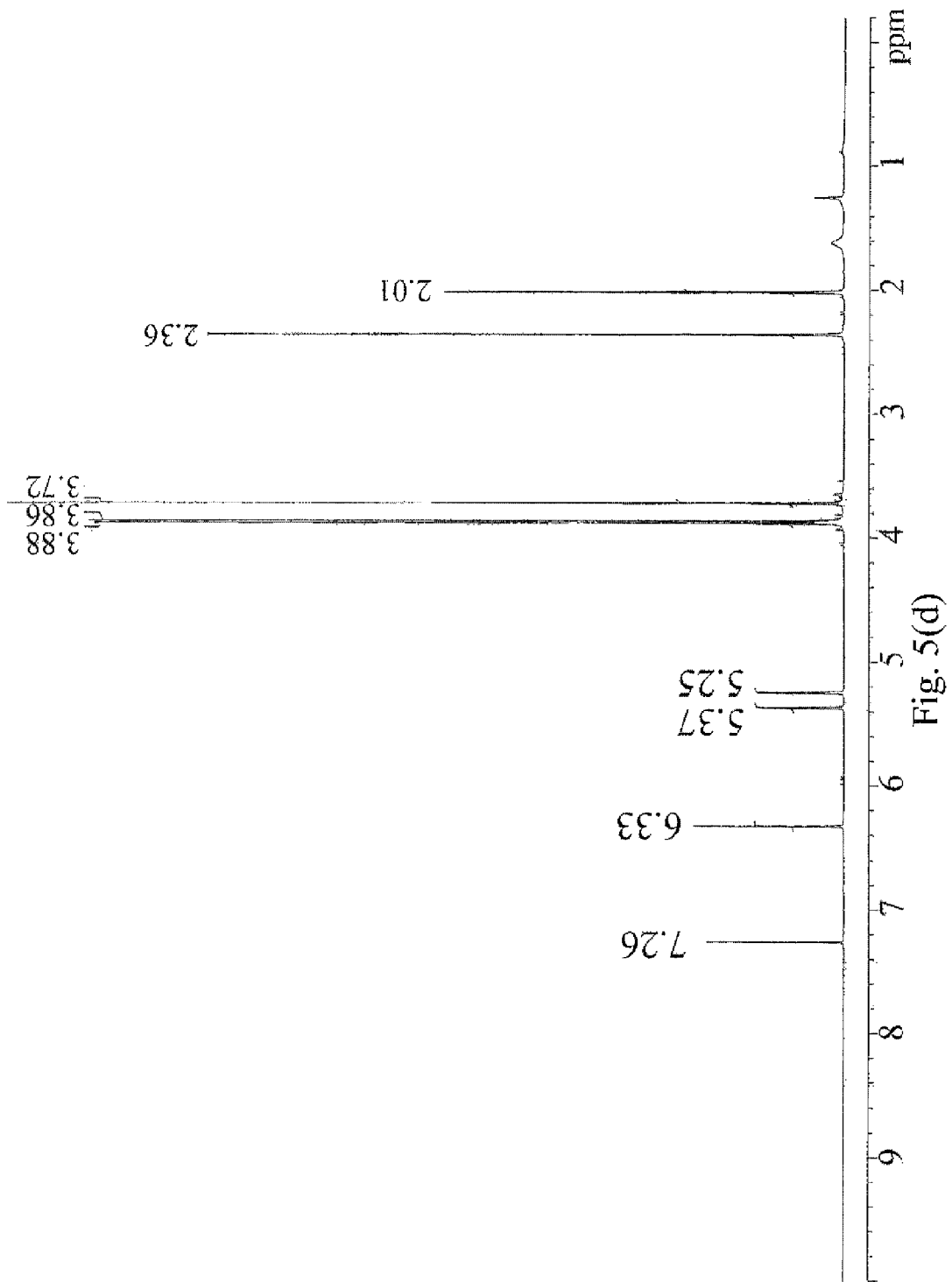

The n-hexane extract and compounds 1 to 3 were solved in CDCl$_3$ solution, and their $^1$H NMR spectra were compared. Please refer to FIG. 5(a), it was observed that the methoxy signal of the n-hexane extract was at $\delta_H$ 3.7-4.0, methylenedioxy signal was at $\delta_H$ 5.9-6.0, an aromatic single hydrogen was at $\delta_H$ 6.2-6.4. Please refer to FIGS. 5(b) to 5(d), the characteristic signals presented by the n-hexane extract were consistent with the respective characteristic signals of compounds 1 to 3. From the above experimental analysis, the n-hexane extract not only could be identified to be the benzenoid-concentrating layer, but compounds 1 to 3 also were the major components of this benzenoid-concentrating layer.

EXPERIMENT 6

Detection of Amounts of Benzenoid Compounds with NMR Spectrum

The detection procedures were described as follows. An adequate internal standard was first chosen. This standard must has high purity and high stability, and its characteristic signals in the NMR spectrum are not interfered by the characteristic signals of the analyzed sample. Next, an specific amount of internal standard was added in the sample, an adequate deuterium solvent was selected to perform the NMR spectrum analysis, integral area ratios of characteristic signals of the compound to those of the internal standard were calculated, and the absolute amount of each compound was obtained by introducing the ratio to the absolute amount formula.

NMR method 1. The quantitative analysis of the major compounds 1 to 3 in the n-hexane extract was performed using NMR spectrum analysis in the present invention. The experimental conditions were listed as follows. The n-hexane extract (10.0 mg) was added in the internal standard, pyrazine (0.132 mg), which was solved in CDCl$_3$ solution (0.6 mL) to be the test solvent for the NMR spectrum analysis. The NMR spectrometer was Varian UNITY plus 400 MHz spectrometer, the scanning number was 10 (7 minutes), the width of spectrum was 6002.4 Hz, and the width of intensity impulse was 6.3 micro-second (μs). Furthermore, the start point and end point of the targeted characteristic proton absorption signal of each compound were manually selected to calculate the integral area of peak to be the basis of this quantitative analysis. The whole experiment was made in triplicate, and its relative standard deviation (RSD %) was determined.

Figure 6A:
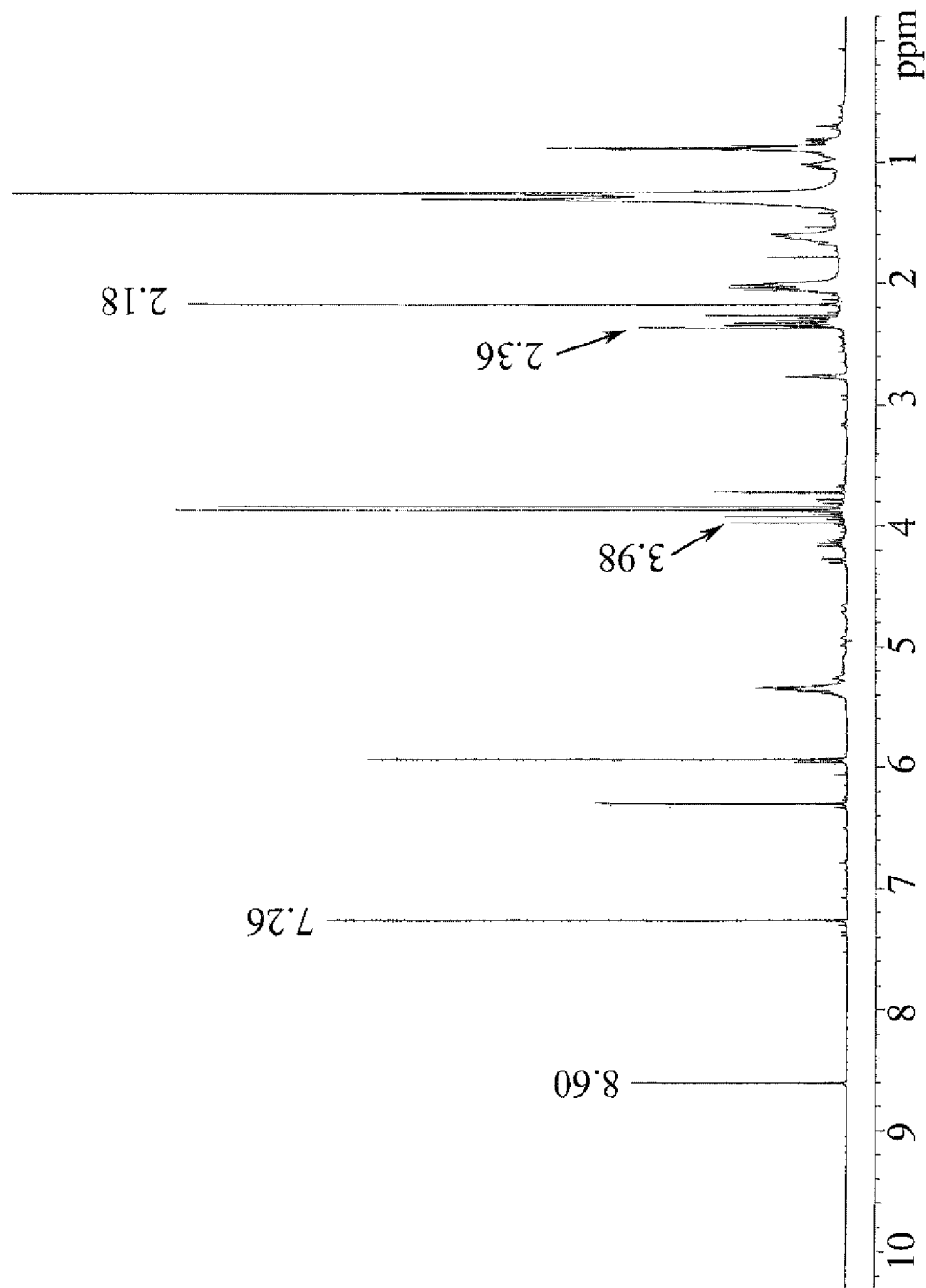
FIGS. 6(a) to 6(d) respectively illustrate (a) the $^1H$ NMR spectra of the n-hexane extract and internal standard (piperazine) solved in the $CDCl_3$ at 400 MHz, (b) the magnification diagram of target characteristics of compound 1 in NMR method 1, (c) the magnification diagram of target characteristics of compounds 2 and 3 in NMR method 1 and (d) the magnification diagram of target characteristics of compounds 1, 2 and 3 in NMR method 2.
Figure 6B:
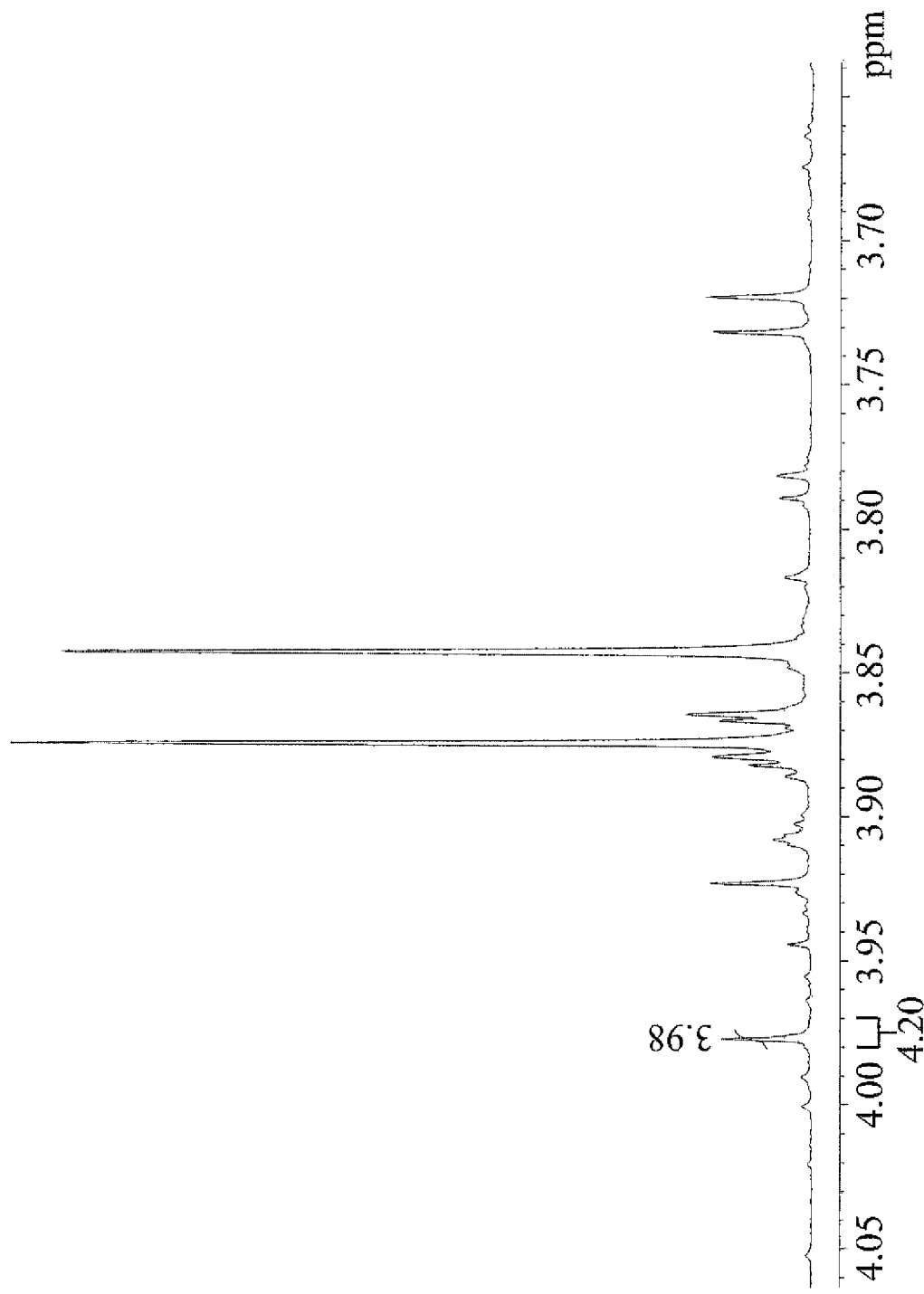
Figure 6C:
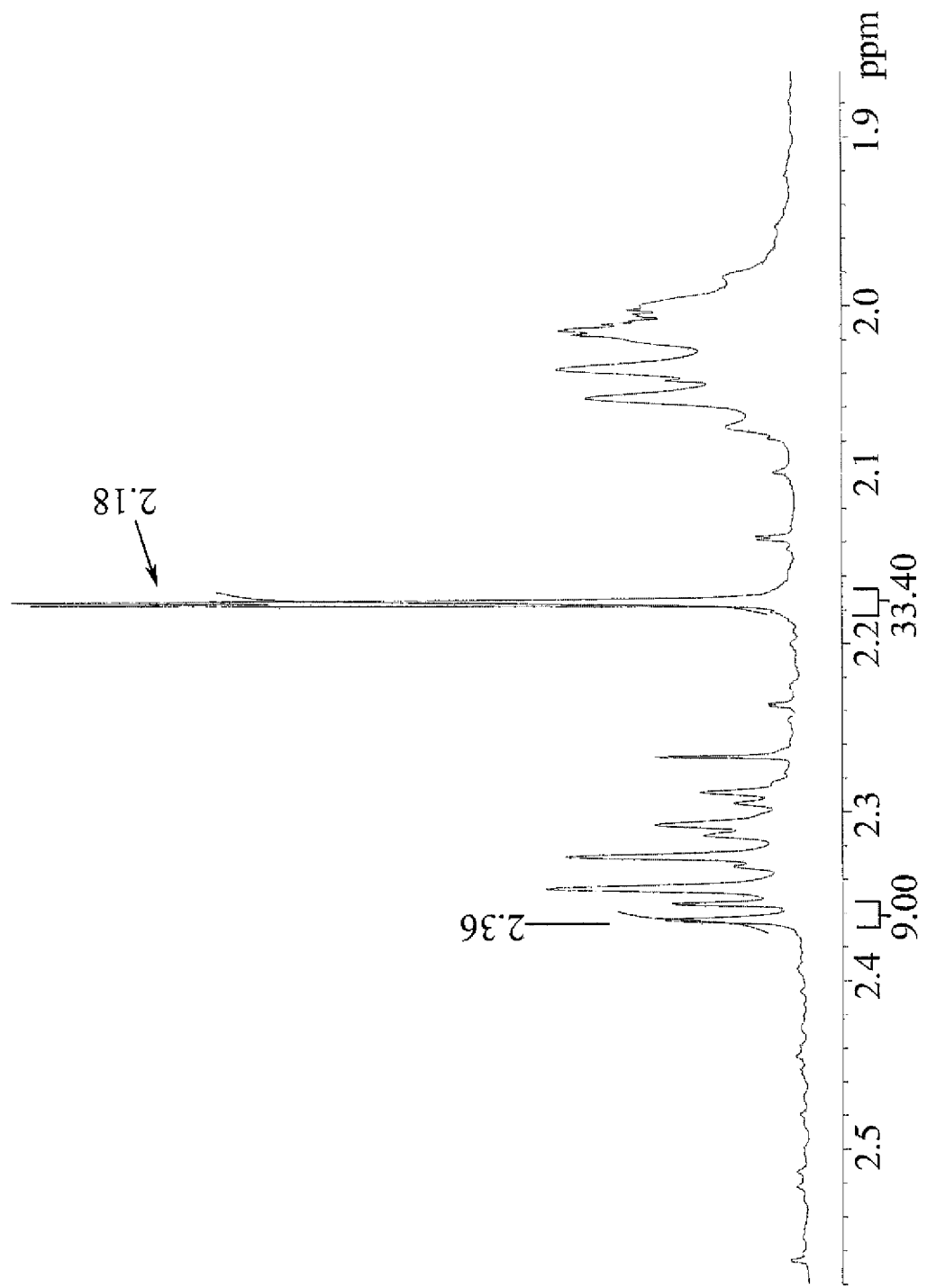

By the $^1$H NMR spectrum signals of three major compounds obtained in Experiment 4, the characteristic proton signals, methoxy signal at $\delta_H$ 3.98 (3H, s) at C-4 of compound 1, methyl signal at $\delta_H$ 2.18 (3H, d, J=0.6 Hz) at C-5 of compound 2 and methyl signal at $\delta_H$ 2.36 (3H, s) at C-3 of compound 3, of the respective compounds were chosen to be the targeted characteristic signals. Please refer to FIGS. 6(a) to 6(c), the integral area ratios of the respective targeted characteristic signals of compounds 1 to 3 to the characteristic signals of the internal standard was respectively determined on the bases of the integral area of characteristic signal ($\delta_H$ 8.60) of the internal standard. The results were referred to Table 2.

TABLE 2

| Integral area ratio of $^1$H NMR characteristic signals of each compound to those of internal standard (in triplicate). | | | | |
|---|---|---|---|---|
| | Targeted | | Integral area ratio | | |
| Compound | characteristic signal | $\delta_H$ (J in Hz) | Experiment 1 | Experiment 2 | Experiment 3 |
| 1 | 4-OCH$_3$ | 3.98 s | 0.42 | 0.41 | 0.40 |
| 2 | 5-CH$_3$ | 2.18 d (0.6) | 3.34 | 3.50 | 3.38 |
| 3 | 3-CH$_3$ | 2.36 s | 0.90 | 0.94 | 0.92 |

The integral area ratio was introduced to the following quantitative formula 1 to determine the amount of compounds 1 to 3 in the n-hexane extract.

$$\left[\frac{(0.22 \text{ mg}/80) \times B \times A}{H}\right] \times MW \quad \text{(Quantitative formula 1)}$$

Eighty (80) is referred to the molecular weight of the internal standard (pyrazine). A is indicated to the integral area ratio of targeted characteristic signals of compounds 1 to 3 to characteristic signals of internal standard. B is referred to the number of proton of internal standard (the number of proton of pyrazine is 4). H is referred to the number of proton in the characteristic signal of compounds 1 to 3 (the targeted characteristic signal of compound 1 is 4-OCH$_3$ and H value is 3; that of compound 2 is 5-CH$_3$ and H value is 3; and that of compound 3 is 3-CH$_3$ and H value is 3). MW is referred to molecular weight of each compound (molecular weights of compounds 1, 2 and 3 were 260, 196 and 246 respectively).

The absolute amount and the RSD % of compounds 1 to 3 of the n-hexane extract in the experiment were obtained from the above-mentioned detection method. Please refer to Table 3, the RSD value in triplicate were at the acceptable range, and it could be known that compounds 1 to 3 were the major components in the n-hexane extract and also were the major components of the benzenoid compounds of the fruiting body of AC.

TABLE 3

Amount of each compound in the n-hexane extract (in triplicate)

| Compound | Amount (weight per 10 mg n-hexane extract) | | | | |
|---|---|---|---|---|---|
| | Experiment 1 | Experiment 2 | Experiment 3 | Average | RSD |
| 1 | 0.40 mg | 0.39 mg | 0.38 mg | 0.39 mg | 2.6% |
| 2 | 2.40 mg | 2.51 mg | 2.42 mg | 2.44 mg | 2.4% |
| 3 | 0.81 mg | 0.85 mg | 0.83 mg | 0.83 mg | 2.4% |

Figure 6D:
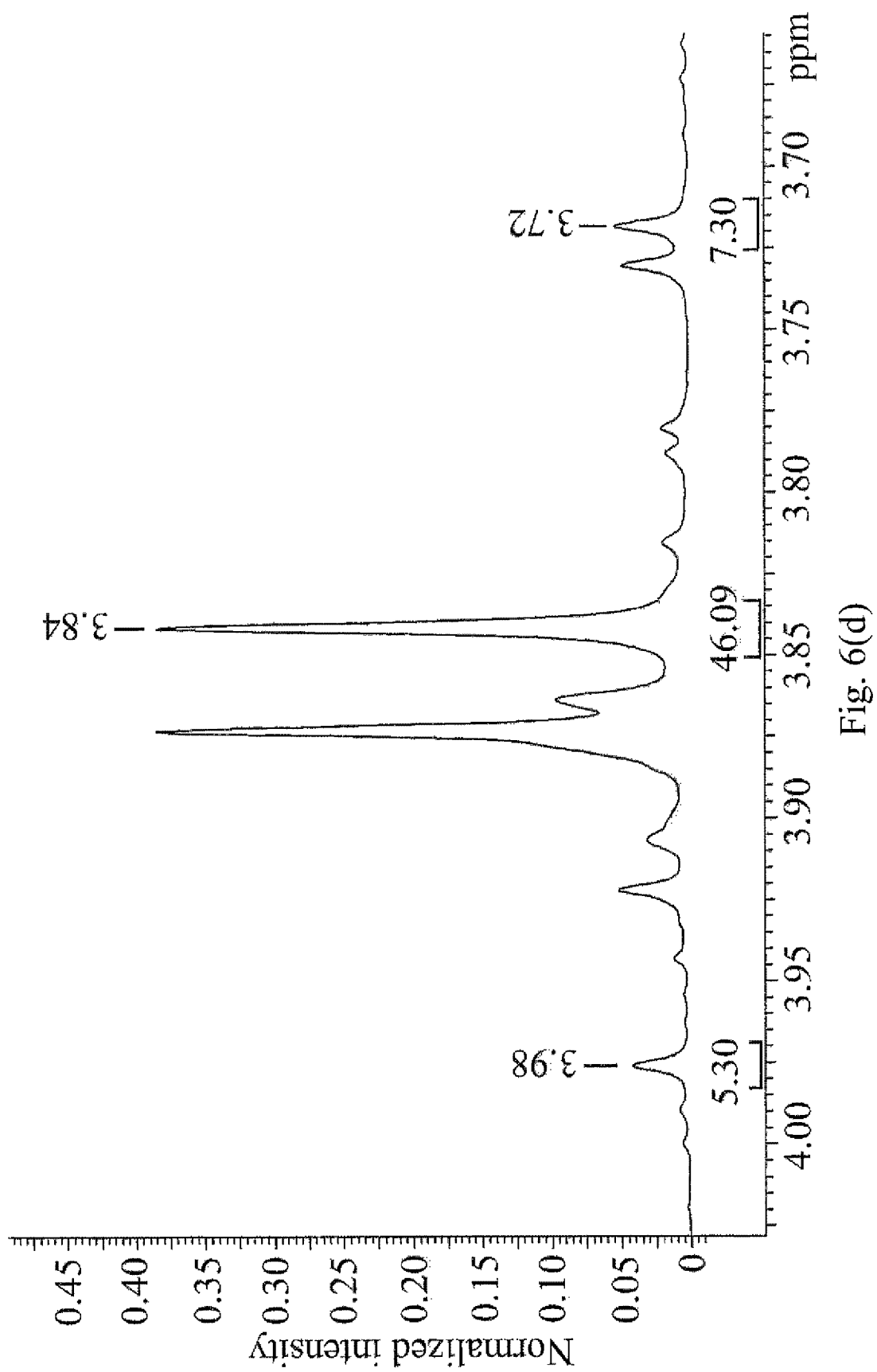

NMR method 2. By the $^1$H NMR spectrum signals of three major compounds obtained in Experiment 4, the characteristic proton signals, methoxy signal at $\delta_H$ 3.98 (3H, s) at C-4 of compound 1, methoxy signal at $\delta_H$ 3.84 (3H, s) at C-7 of compound 2 and methoxy signal at $\delta_H$ 3.72 (3H, s) at C-2 of compound 3, of the respective compounds were chosen to be the targeted characteristic signals. Please refer to FIG. 6(d), the integral area ratios of the respective targeted characteristic signals of compounds 1 to 3 to the characteristic signals of the internal standard was respectively determined on the bases of the integral area of characteristic signal ($\delta_H$ 8.60) of the internal standard. The results were referred to Table 4.

TABLE 4

Integral area ratio of $^1$H NMR characteristic signals of each compound to those of internal standard (in triplicate).

| Compound | Targeted characteristic signal | $\delta_H$ (J in Hz) | Integral area ratio | | |
|---|---|---|---|---|---|
| | | | Experiment 1 | Experiment 2 | Experiment 3 |
| 1 | 4-OCH$_3$ | 3.98 s | 0.53 | 0.51 | 0.51 |
| 2 | 7-OCH$_3$ | 3.84 s | 4.61 | 4.62 | 4.61 |
| 3 | 2-OCH$_3$ | 3.72 s | 0.73 | 0.75 | 0.74 |

The integral area ratio was introduced to the following quantitative formula 1 to determine the amount of compounds 1 to 3 in the n-hexane extract.

$$\left[\frac{(0.22 \text{ mg}/80) \times B \times A}{H}\right] \times MW \quad \text{(Quantitative formula 1)}$$

Eighty (80) is referred to the molecular weight of the internal standard (pyrazine). A is indicated to the integral area ratio of targeted characteristic signals of compounds 1 to 3 to characteristic signals of internal standard. B is referred to the number of proton of internal standard (the number of proton of pyrazine is 4). H is referred to the number of proton in the characteristic signal of compounds 1 to 3 (the targeted characteristic signal of compound 1 is 4-OCH$_3$ and H value is 3; that of compound 2 is 7-OCH$_3$ and H value is 3; and that of compound 3 is 2-OCH$_3$ and H value is 3). MW is referred to molecular weight of each compound (molecular weights of compounds 1, 2 and 3 were 260, 196 and 246 respectively).

The absolute amount and the RSD % of compounds 1 to 3 of the n-hexane extract in the experiment were obtained from the above-mentioned detection method. Please refer to Table 5, the RSD value in triplicate were at the acceptable range, and it could be known that compounds 1 to 3 were the major components in the n-hexane extract and also were the major components of the benzenoid compounds of the fruiting body of AC.

TABLE 5

Amount of each compound in the n-hexane extract (in triplicate)

| Compound | Amount (weight per 10 mg n-hexane extract) | | | | |
|---|---|---|---|---|---|
| | Experiment 1 | Experiment 2 | Experiment 3 | Average | RSD |
| 1 | 0.50 mg | 0.49 mg | 0.49 mg | 0.49 mg | 1.2% |
| 2 | 3.31 mg | 3.32 mg | 3.31 mg | 3.31 mg | 0.2% |
| 3 | 0.66 mg | 0.68 mg | 0.67 mg | 0.67 mg | 1.4% |

EXPERIMENT 7

Amount Detection of the Benzenoid Compounds with HPLC

HPLC method 1. The relative amount analysis of the major components in the n-hexane extract was performed using HPLC, and the HPLC spectra of three obtained major compounds 1 to 3 were compared with that of the n-hexane extract. The conditions for HPLC were listed as follows. HPLC was Shimadzu LC-10AT, detector was Shimadzu SPD-M10A photodiode array detector, the auto sampler was Shimadzu SIL-20A prominence auto sampler; the HPLC column was Cosmosil 5C-18-MS (250×4.6 mm, 5 µm); solvents A and B in the mobile phase respectively were acetonitrile and water, flow rate was 1 ml/min, the temperature of column was room temperature, and the detection wavelength was 254 nm and 270 nm. The conditions of the solvent system were listed as follows. The mobile phase included solvents A and B, the linear gradient was 30% A to 100% A within 0 to 60 minutes, and the flow rate and the temperature of column were described as above.

Figure 7A:
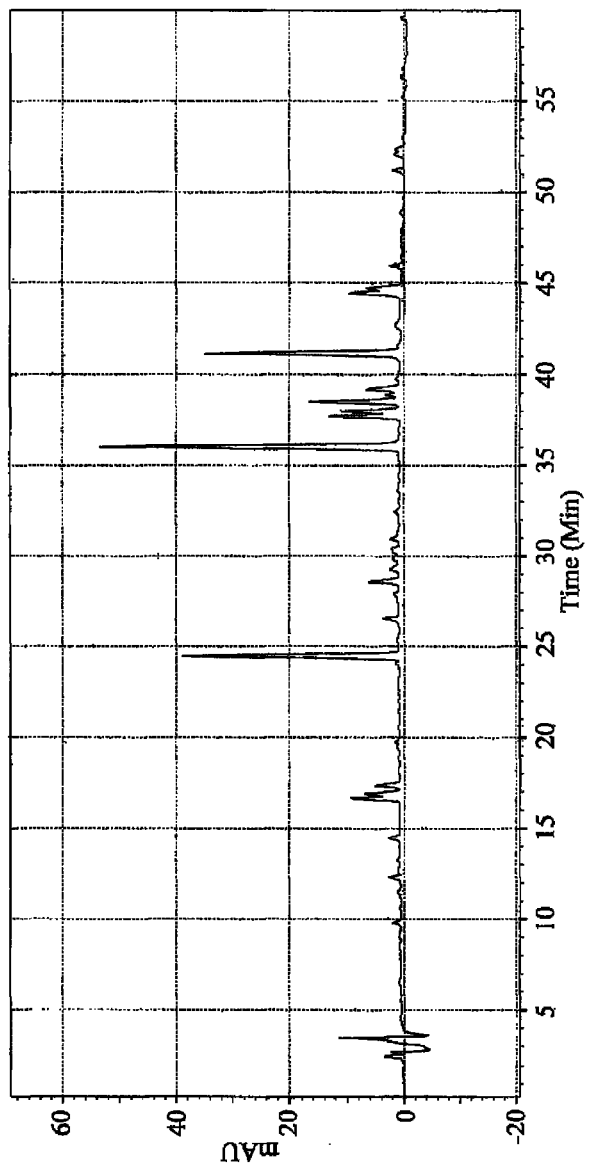
FIGS. 7(a) and 7(b) respectively illustrate the HPLC spectra of (a) the n-hexane extract and (b) compounds 1 to 3 at 254 nm in HPLC method 1.
Figure 7B:
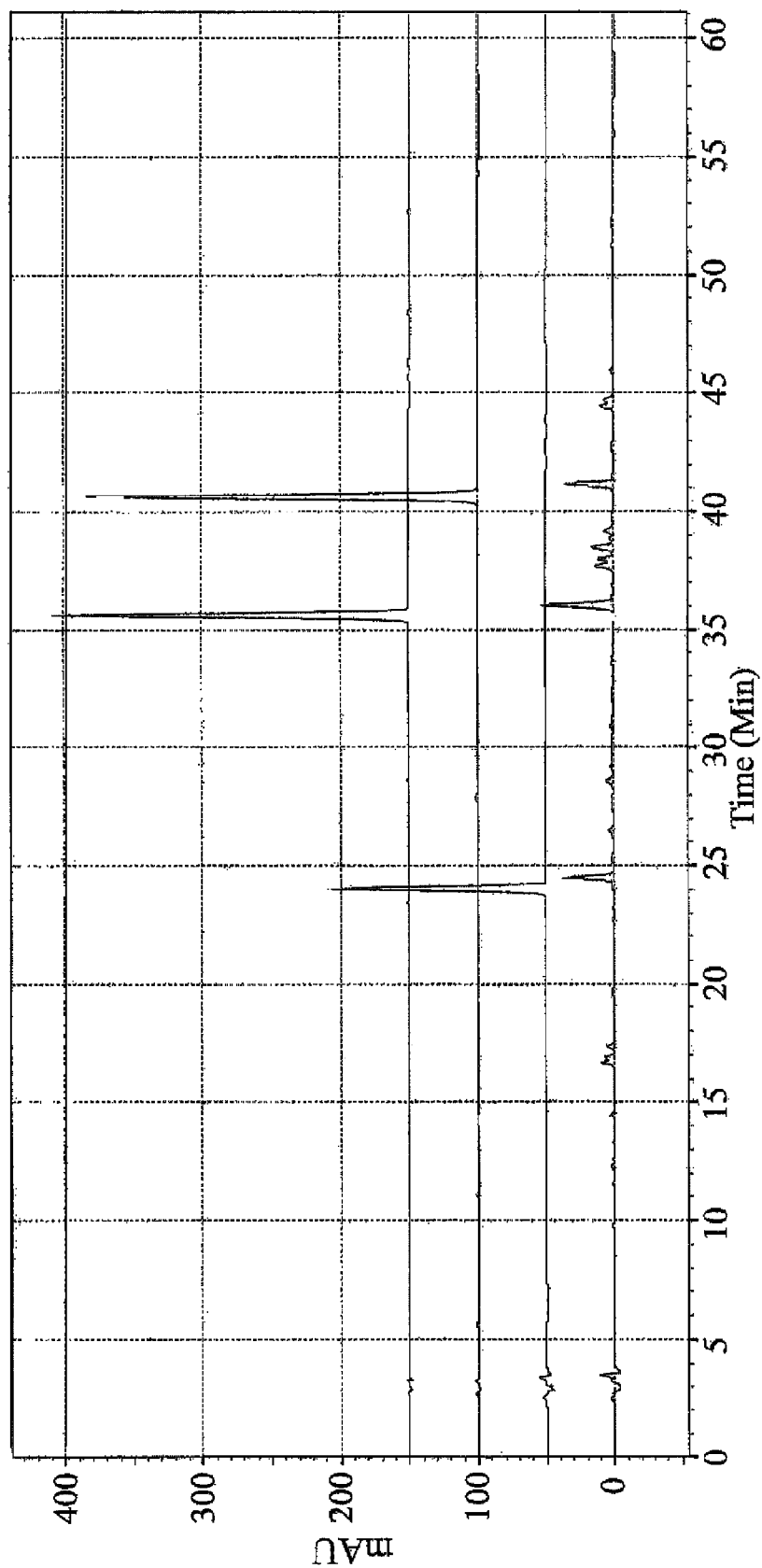

Please refer to FIGS. 7(a) and 7(b) and Table 6, which are the comparisons of area percentage and height percentage of each component in the n-hexane extract using HPLC at 254 nm. At the wavelength of 254 nm, retention time of 41.149, 24.489 and 36.006 minutes respectively were indicated to the chromatographic peaks of compounds 1 to 3. The area percentages of three compounds respectively were 16.91%, 17.30% and 24.87% with a total of 59.08%, and the height percentage thereof respectively were 15.90%, 17.62% and 24.30% with a total of 57.82%. Therefore, it could be known that compounds 1 to 3 were the major components in the n-hexane extract of the fruiting body of AC and also were the major components in the benzenoid compounds thereof.

TABLE 6

Comparisons of area percentage and height percentage of each component in the n-hexane extract using HPCL at 254 nm

| Product | Retention Time (Min) | Area (%) | Height (%) |
|---|---|---|---|
| Compound 1 | 41.149 | 16.91 | 15.90 |
| Compound 2 | 24.489 | 17.30 | 17.62 |
| Compound 3 | 36.006 | 24.87 | 24.30 |
| Others | | 40.92 | 42.18 |
| Total | | 100.00 | 100.00 |

Figure 8A:
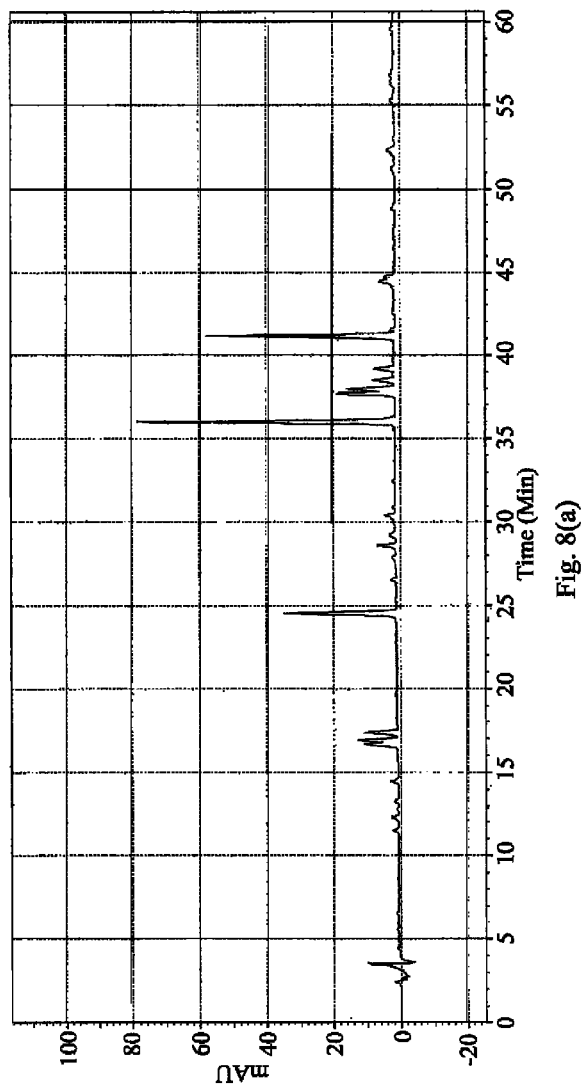
FIGS. 8(a) and 8(b) respectively illustrate the HPLC spectra of (a) n-hexane extract and (b) compounds 1 to 3 at 270 nm in HPLC method 1.
Figure 8B:
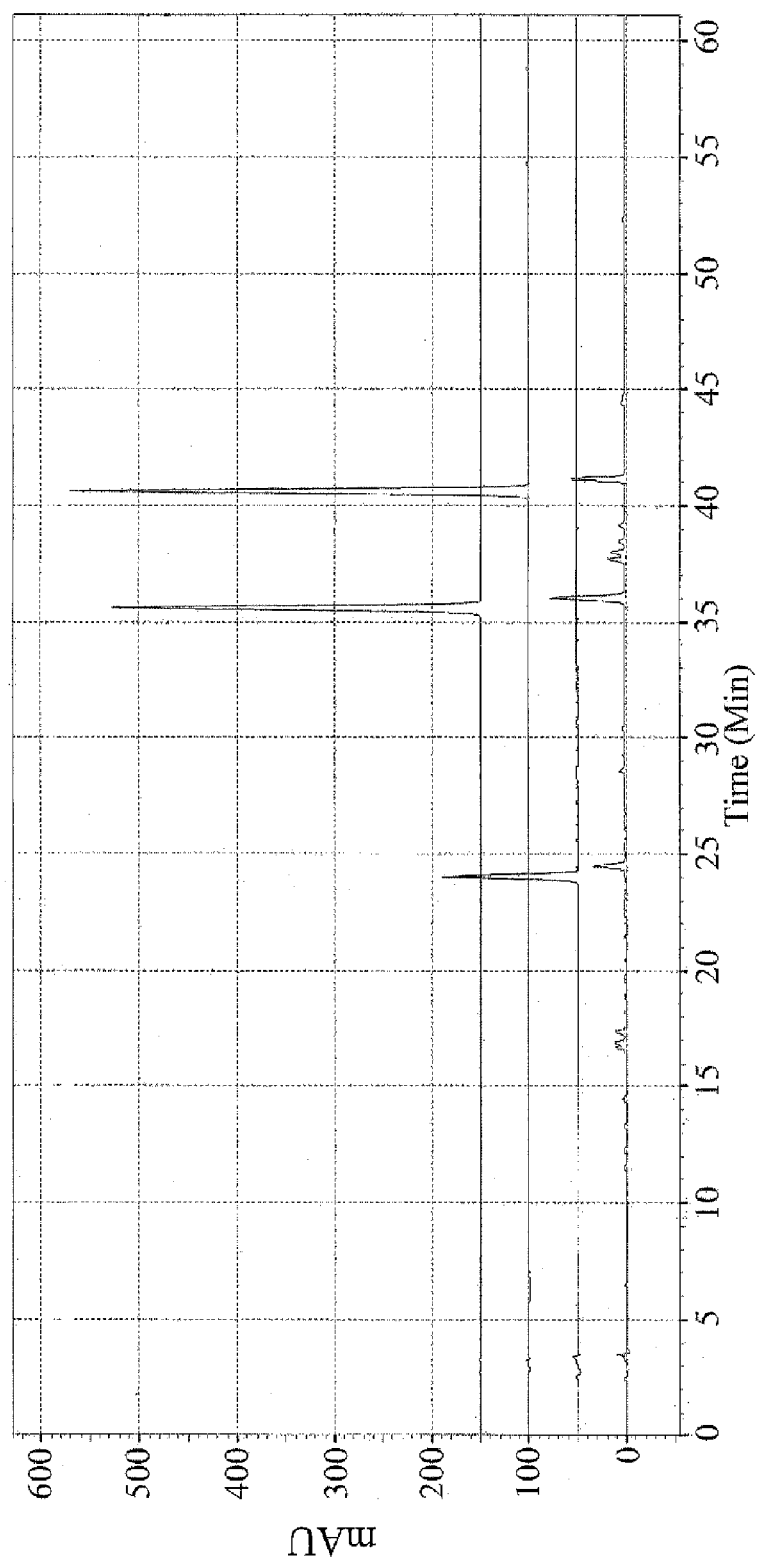

Please refer to FIGS. 8(a) and 8(b) and Table 7, which are the comparisons of area percentage and height percentage of each component in the n-hexane extract using HPLC at 270 nm. At the wavelength of 270 nm, retention time of 41.149, 24.489 and 36.006 minutes respectively were indicated to the chromatographic peaks of compounds 1 to 3. The area percentages of three compounds respectively were 16.97%, 11.50% and 25.54% with a total of 54.01%, and the height percentages thereof respectively were 19.81%, 12.52% and 27.00% with a total of 59.33%. Therefore, it could be known that compounds 1 to 3 were the major components in the n-hexane extract of the fruiting body of AC and also were the major components in the benzenoid compounds thereof.

TABLE 7

Comparisons of area percentage and height percentage of each component in the n-hexane extract using HPLC at 270 nm

| Product | Retention time (Min) | Area (%) | Height (%) |
|---|---|---|---|
| Compound 1 | 41.149 | 16.97 | 19.81 |
| Compound 2 | 24.489 | 11.50 | 12.52 |
| Compound 3 | 36.006 | 25.54 | 27.00 |
| Others | | 45.99 | 40.67 |
| Total | | 100.00 | 100.00 |

HPLC method 2. The relative amount analysis of the major components in the n-hexane extract was performed using HPLC, and the HPLC spectra of three obtained major compounds 1 to 3 were compared with that of the n-hexane extract. The conditions for HPLC were listed as follows. HPLC was Shimadzu LC-10AT, detector was Shimadzu SPD-M10A photodiode array detector, the auto sampler was Shimadzu SIL-20A prominence auto sampler; the HPLC column was Agilent Poroshell 120 SB-C18 (150×4.6 mm, 2.7 µm); solvents A and B in the mobile phase respectively were acetonitrile and water (contain 0.1 formic acid), flow rate was 1.2 ml/min, the temperature of column was room temperature, and the detection wavelength was 254 nm and 270 nm. The conditions of the solvent system were listed as follows. The mobile phase included solvents A and B, the gradient program was used as follows: the initial elution condition was A-B (47:53, v/v), linearly changed to A-B (55:45, v/v) at 10.5 min and held for 4.5 min, then linearly changed to A-B (85:15, v/v) at 20 min, A-B (100:0, v/v) from 20 min to 23 min. Over the next 7 min, the percentage of mobile phase A kept in 100%., and the flow rate and the temperature of column were described as above.

Figure 9A:
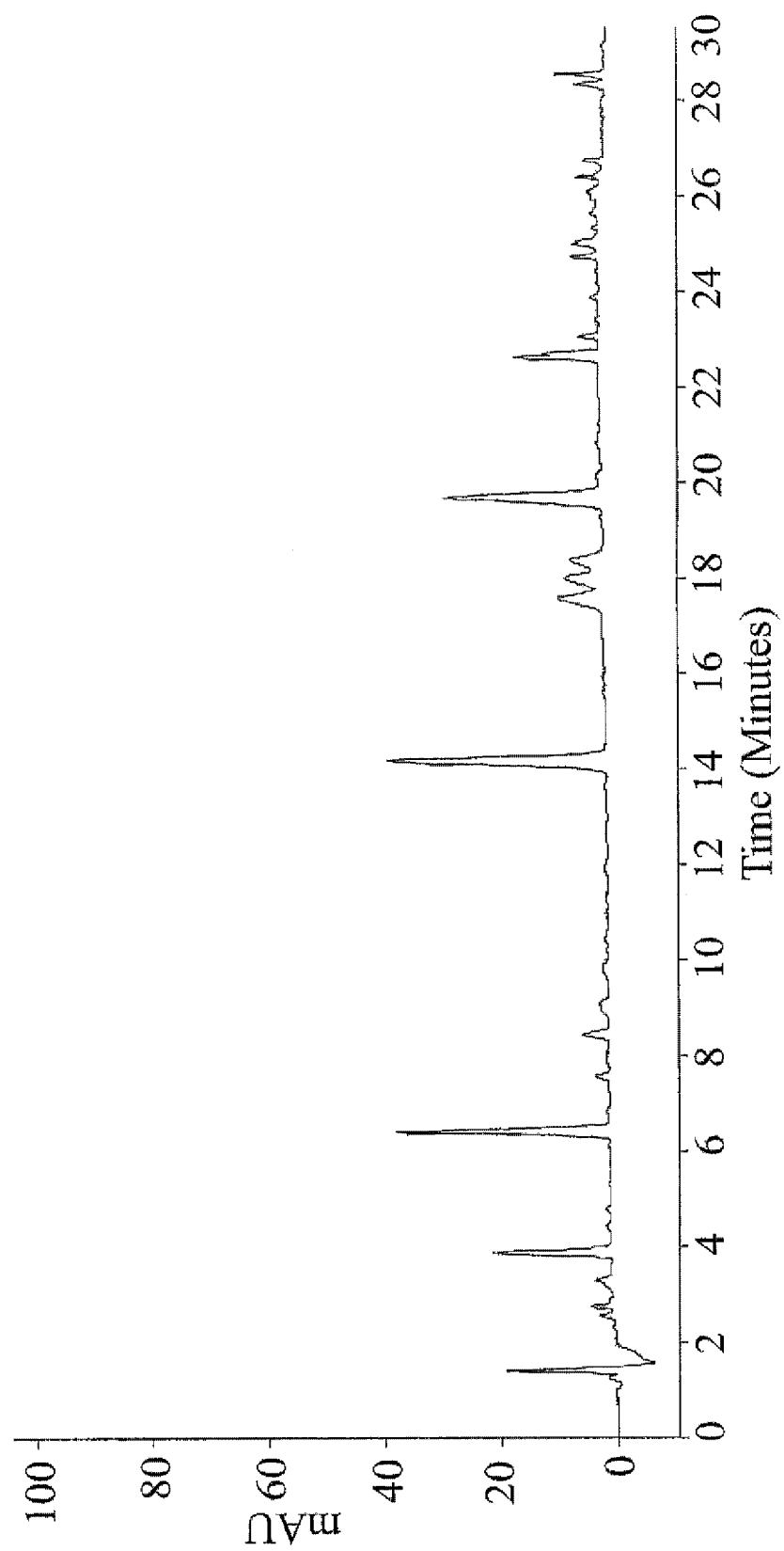
FIGS. 9(a) and 9(b) respectively illustrate the HPLC spectra of n-hexane extract at (a) 254 nm and (b) 270 nm in HPLC method 2.

Please refer to FIG. 9(a) and Table 8, which are the comparisons of area percentage and height percentage of each component in the n-hexane extract using HPLC at 254 nm. At the wavelength of 254 nm, retention time of 19.701, 6.434 and 14.193 minutes respectively were indicated to the chromatographic peaks of compounds 1 to 3. The area percentages of three compounds respectively were 16.49%, 12.77% and 25.62% with a total of 54.88%, and the height percentage thereof respectively were 15.08%, 19.70% and 20.37% with a total of 55.15%. Therefore, it could be known that compounds 1 to 3 were the major components in the n-hexane extract of the fruiting body of AC and also were the major components in the benzenoid compounds thereof.

TABLE 8

Comparisons of area percentage and height percentage of each component in the n-hexane extract using HPCL at 254 nm

| Product | Retention Time (Min) | Area (%) | Height (%) |
|---|---|---|---|
| Compound 1 | 19.701 | 16.49 | 15.08 |
| Compound 2 | 6.434 | 12.77 | 19.70 |
| Compound 3 | 14.193 | 25.62 | 20.37 |
| Others | | 45.12 | 44.85 |
| Total | | 100.00 | 100.00 |

Figure 9B:
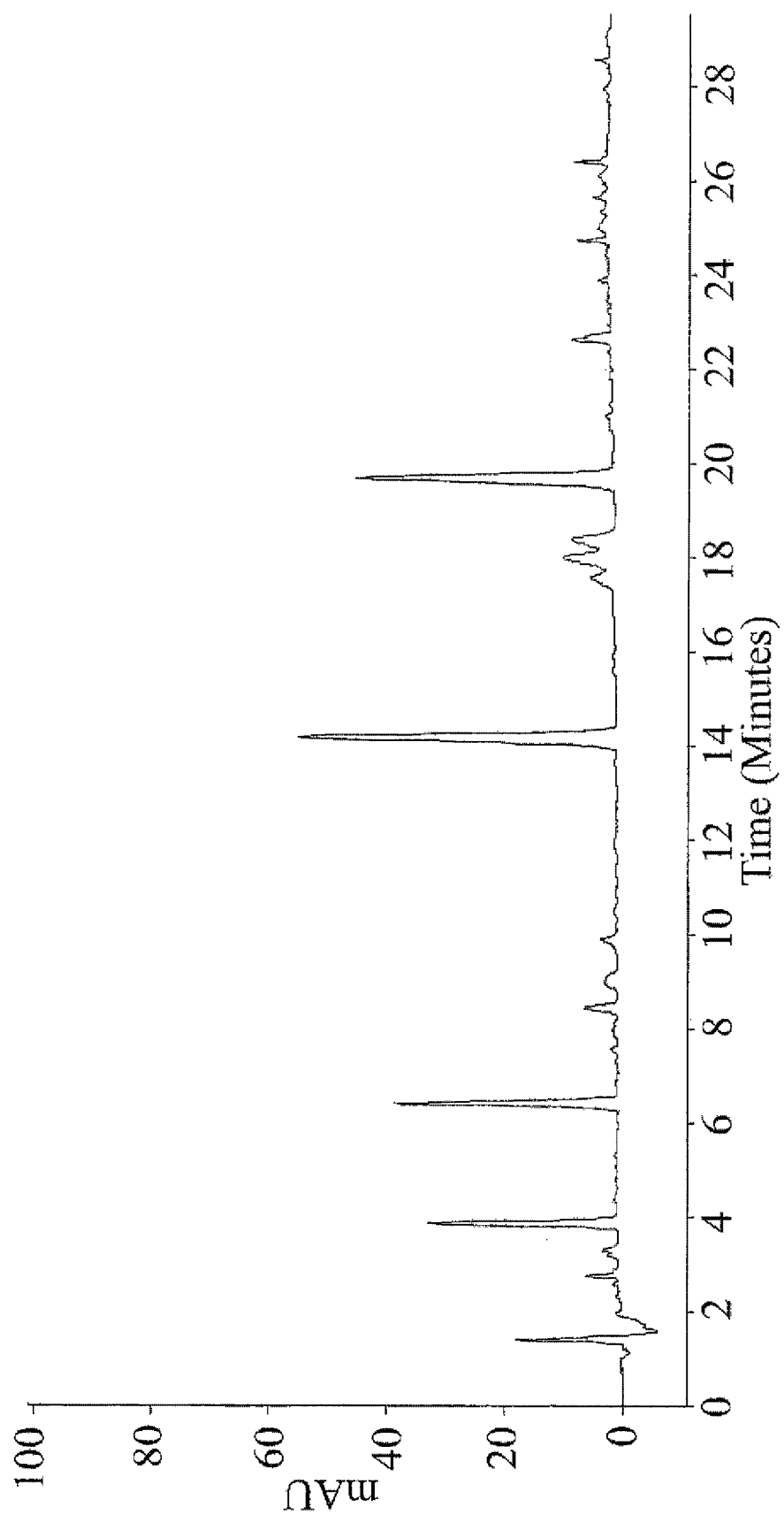

Please refer to FIG. 9(b) and Table 9, which are the comparisons of area percentage and height percentage of each component in the n-hexane extract using HPLC at 270 nm. At the wavelength of 270 nm, retention time of 19.697, 6.434 and 14.193 minutes respectively were indicated to the chromatographic peaks of compounds 1 to 3. The area percentages of three compounds respectively were 25.04%, 14.22% and 32.11% with a total of 71.37%, and the height percentages thereof respectively were 22.31%, 19.29% and 27.41% with a total of 69.01%. Therefore, it could be known that compounds 1 to 3 were the major components in the n-hexane extract of the fruiting body of AC and also were the major components in the benzenoid compounds thereof.

TABLE 9

Comparisons of area percentage and height percentage of each component in the n-hexane extract using HPLC at 270 nm

| Product | Retention time (Min) | Area (%) | Height (%) |
|---|---|---|---|
| Compound 1 | 19.697 | 25.04 | 22.31 |
| Compound 2 | 6.434 | 14.22 | 19.29 |
| Compound 3 | 14.193 | 32.11 | 27.41 |
| Others | | 28.63 | 30.99 |
| Total | | 100.00 | 100.00 |

Additionally, the molecular weights of the major components, i.e. compounds 1 to 3 (standard sample), of the n-hexane extract were determined using high performance liquid chromatography electrospray ionization tandem mass chromatography (HPLC-ESI-MS) with the positive ion mode. The conditions of HPLC were listed as follows. The HPLC meter was Agilent 1100 series, the HPLC column was Cosmosil 5C-18-MS 250×4.6 mm, the solvents A and B in the mobile phase respectively were acetonitrile and 0.1% formic acid $H_2O$, flow rate was 1 ml/min, the temperature of column was room temperature, and the detection wavelengths were 254 nm and 270 nm. The conditions of the solvent system were listed as follows. The mobile phase included solvents A and B, the linear gradient was 30% A to 100% A within 0 to 60 minutes, and flow rate and column temperature were described as above. The mass spectrometer was Thermo Finnigan LCQ DECA XP$^{plus}$. The retention time of compound 1 was 38.22 minutes, its major ion peak was at m/z 197 [M+H]$^+$, and the determined molecular weight (MW) of compound 1 was 260. The retention time of compound 2 was 22.39 minutes, its major ion peak was at m/z 247 [M+H]$^+$, and the determined MW of compound 3 was 246.

It could be known from the results of the above NMR analysis and HPLC-ESI-MS analysis that 4,7-dimethoxy-5-(3-methylbut-3-en-1-ynyl)-6-methyl-1,3-benzodioxole (compound 1), 4,7-dimethoxy-5-methyl-1,3-benzodioxole (compound 2) and 1,2,5-trimethoxy-3-methyl-4-(3-methylbut-3-en-1-ynyl)benzene (compound 3) were the major components in the n-hexane extract of the fruiting body of *Antrodia cinnamomea*. The forementioned experimental methods could be the good tool for detecting the benzenoid compound in the fruiting body of AC in the industries.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for preparing an n-hexane extract of a fruiting body of an *Antrodia cinnamomea*, comprising steps of:
    providing the fruiting body of the *A. cinnamomea*;
    extracting the fruiting body with an ethanol solution to obtain an ethanol extract; and
    extracting the ethanol extract with an n-hexane solution to obtain the n-hexane extract comprising at least one benzenoid compound.

2. The method according to claim 1, wherein the at least one benzenoid compound is one selected from a group consisting of a 4,7-dimethoxy-5-(3-methylbut-3-en-1-ynyl)-6-methyl-1,3-benzodioxole, a 4,7-dimethoxy-5-methyl-1,3-benzodioxole, an antrocamphine A and a combination thereof.

3. The method according to claim 1 further comprising a step of: grinding the fruiting body.

4. A method for detecting an amount of at least one benzenoid compound in a fruiting body of an *Antrodia cinnamomea*, comprising steps of:
    providing an n-hexane extract extracted from the fruiting body;
    detecting whether the at least one benzenoid compound is present in the n-hexane extract with a $^1$H nuclear magnetic resonance ($^1$H NMR); and
    detecting the amount by using a high performance liquid chromatography (HPLC) when the at least one benzenoid compound is present in the n-hexane extract.

5. The method according to claim 4 further comprising steps of:
    extracting the fruiting body with an ethanol solution to obtain an ethanol extract; and
    extracting the ethanol extract with an n-hexane solution to obtain the n-hexane extract.

6. The method according to claim 4 further comprising a step of: detecting a signal of the at least one benzenoid compound with the $^1$H NMR, wherein the signal is one selected from a group consisting of aromatic signals, a double bond signal, a methoxy signal, a methyl signal and a combination thereof.

7. The method according to claim 6, wherein the aromatic signals are ranged at δ 6.4 to 6.6 and δ 5.8 to 6.1, the double bond signal is ranged at δ 5.4 to 5.6, the methoxy signal is ranged at δ 3.7 to 4.1 and the methyl signal is ranged at δ 2.1 to 2.6 when the n-hexane extract is solved in a pyridine-D5 ($C_5D_5N$).

8. The method according to claim 4, wherein the HPLC comprises a detector, and the detector is one selected from a group consisting of a full wavelength detector, a single wavelength detector, an electrospray ionization mass spectrometer and a combination thereof.

9. The method according to claim 8, wherein the full wavelength detector is configured to detect wavelengths at 254 nm and 270 nm.

10. A method for detecting an amount of at least one benzenoid compound in an n-hexane extract of a fruiting body of an *Antrodia cinnamomea* with a $^1$H nuclear magnetic resonance ($^1$H NMR) based on an internal standard corresponding to the n-hexane extract, the method comprising steps of:
    detecting whether a methoxy signal ranged at δ 3.9 to 4.0 exists in the n-hexane extract;
    detecting whether a first methyl signal ranged at δ 2.1 to 2.2 exists in the n-hexane extract; and
    detecting whether a second methyl signal ranged at δ 2.3 to 2.4 exists in the n-hexane extract.

11. The method according to claim 10, where the methoxy signal, the first methyl signal and the second methyl signal are respectively present to indicate that the n-hexane extract comprises a 4,7-dimethoxy-5-(3-methylbut-3-en-1-ynyl)-6-methyl-1,3-benzodioxole, a 4,7-dimethoxy-5-methyl-1,3-benzodioxole and an antrocamphine A.

12. The method according to claim 11, wherein the methoxy signal, the first methyl signal and the second methyl signal respectively have a first intensity, a second intensity and a third intensity, the internal standard is a pyrazine, the first intensity is calculated based on the pyrazine when the methoxy signal is present, the second intensity is calculated based thereon when the first methyl signal is present, the third intensity is calculated based thereon when the second methyl signal is present, and amounts of a 4,7-dimethoxy-5-(3-methylbut-3-en-1-ynyl)-6-methyl-1,3-benzodioxole, a 4,7-dimethoxy-5-methyl-1,3-benzodioxole and an antrocamphine A in the n-hexane extract are determined by the first, the second and the third intensities.

13. A method for detecting an amount of at least one benzenoid compound in an n-hexane extract of a fruiting body of an *Antrodia cinnamomea* with a $^1$H nuclear magnetic resonance ($^1$H NMR) based on an internal standard corresponding to the n-hexane extract, the method comprising steps of:
    detecting whether a first methoxy signal ranged at δ 3.9 to 4.0 exists in the n-hexane extract;
    detecting whether a second methoxy signal ranged at δ 3.8 to 3.9 exists in the n-hexane extract; and
    detecting whether a third methoxy signal ranged at δ 3.7 to 3.8 exists in the n-hexane extract.

14. The method according to claim 13, where the first methoxy signal, the second methoxy signal and the third methoxy signal are respectively present to indicate that the n-hexane extract comprises a 4,7-dimethoxy-5-(3-methylbut-3-en-1-ynyl)-6-methyl-1,3-benzodioxole, a 4,7-dimethoxy-5-methyl-1,3-benzodioxole and an antrocamphine A.

15. The method according to claim 14, wherein the first methoxy signal, the second methoxy signal and the third methoxy signal respectively have a first intensity, a second intensity and a third intensity, the internal standard is a pyrazine, the first intensity is calculated based on the pyrazine when the first methoxy signal is present, the second intensity is calculated based thereon when the second methoxy signal is present, the third intensity is calculated based thereon when the third methoxy signal is present, and amounts of a 4,7-dimethoxy-5-(3-methylbut-3-en-1-ynyl)-6-methyl-1,3-benzodioxole, a 4,7-dimethoxy-5-methyl-1,3-benzodioxole and an antrocamphine A in the n-hexane extract are determined by the first, the second and the third intensities.

16. A detecting method comprising a step of simultaneously detecting amounts of a 4,7-dimethoxy-5-(3-methylbut-3-en-1-ynyl)-6-methyl-1,3-benzodioxole, a 4,7-dimethoxy-5-methyl-1,3-benzodioxole and an antrocamphine A with a high performance liquid chromatography (HPLC).

17. A detecting method comprising a step of simultaneously detecting amounts of a 4,7-dimethoxy-5-(3-methylbut-3-en-1-ynyl)-6-methyl-1,3-benzodioxole, a 4,7-dimethoxy-5-methyl-1,3-benzodioxole and an antrocamphine A with a $^1$H nuclear magnetic resonance ($^1$H NMR).

18. A method for isolating at least one benzenoid compound comprising a 4,7-dimethoxy-5-(3-methylbut-3-en-1-ynyl)-6-methyl-1,3-benzodioxole from a fruiting body of an *Antrodia cinnamomea*, comprising steps of:
   providing an n-hexane extract extracted from the fruiting body;
   chromatographing the n-hexane extract with a silica gel and a plurality of n-hexane-ethyl acetate gradients to obtain at least two fractions having a first portion and a second portion eluted later than the first portion;
   chromatographing the first portion with a first Sephadex resin and a first ethyl acetate-dichloromethane (EtAc—CH$_2$Cl$_2$) solution to obtain a plurality of first sub-fractions;
   chromatographing each of the plurality of first sub-fractions with a first prepared thin layered chromatography and an n-hexane-ethyl acetate solution to obtain a first sub-fraction product; and
   purifying the first sub-fraction product with a first octadecylsilane (ODS) high performance reverse chromatography to obtain the 4,7-dimethoxy-5-(3-methylbut-3-en-1-ynyl)-6-methyl-1,3-benzodioxole.

19. The method according to claim 18, wherein the at least one benzenoid compound further comprises a 4,7-dimethoxy-5-methyl-1,3-benzodioxole obtained in the purifying step.

20. The method according to claim 18, wherein the at least one benzenoid compound further comprises an antrocamphine A, the method further comprises steps of:
   chromatographing the second portion with a second Sephadex resin and a second EtAc—CH$_2$Cl$_2$ solution to obtain a plurality of second sub-fractions; and
   chromatographing each of the plurality of second sub-fractions with a prepared thin layered chromatography and a dichloromethane solution to obtain the antrocamphine A.

21. The method according to claim 16, wherein the method further comprises steps of:
   extracting the fruiting body with an ethanol solution to obtain an ethanol extract;
   extracting the ethanol extract with an n-hexane solution to obtain the n-hexane extract.

22. The method according to claim 5, wherein the at least one benzenoid compound is one selected from a group consisting of a 4,7-dimethoxy-5-(3-methylbut-3-en-1-ynyl)-6-methyl-1,3-benzodioxole, a 4,7-dimethoxy-5-methyl-1,3-benzodioxole, an antrocamphine A and a combination thereof.

* * * * *